United States Patent
Fischell et al.

(10) Patent No.: US 11,491,313 B2
(45) Date of Patent: Nov. 8, 2022

(54) GUIDE CATHETER EXTENSION SYSTEM WITH A DELIVERY MICRO-CATHETER CONFIGURED TO FACILITATE PERCUTANEOUS CORONARY INTERVENTION

(71) Applicant: CROSSLINER, INC., Kalamazoo, MI (US)

(72) Inventors: Tim A. Fischell, Kalamazoo, MI (US); Frank S. Saltiel, Willowbrook, IL (US)

(73) Assignee: CROSSLINER, INC., Kalamazoo, MI (US)

( * ) Notice: Subject to any disclaimer, the term of this patent is extended or adjusted under 35 U.S.C. 154(b) by 0 days.

(21) Appl. No.: 15/899,603

(22) Filed: Feb. 20, 2018

(65) Prior Publication Data

US 2019/0255297 A1 Aug. 22, 2019

(51) Int. Cl.
*A61M 25/09* (2006.01)
*A61M 25/10* (2013.01)
(Continued)

(52) U.S. Cl.
CPC .... *A61M 25/0905* (2013.01); *A61M 25/0169* (2013.01); *A61M 25/09041* (2013.01);
(Continued)

(58) Field of Classification Search
CPC .............. A61M 25/09; A61M 25/0905; A61M 25/0102; A61M 25/0169;
(Continued)

(56) References Cited

U.S. PATENT DOCUMENTS 3,388,703 A * 6/1968 Bowes ................ A61M 25/065
604/166.01
5,102,390 A 4/1992 Crittenden et al.
(Continued)

FOREIGN PATENT DOCUMENTS

WO WO 2019/164592 8/2019
WO WO 2021/167653 8/2021

OTHER PUBLICATIONS

Biometrics, "What are Micro-Catheters?", Sep. 15, 2015 (Year: 2015).*
(Continued)

*Primary Examiner* — Tiffany Legette
*Assistant Examiner* — Antarius S Daniel
(74) *Attorney, Agent, or Firm* — Knobbe, Martens, Olson & Bear, LLP

(57) ABSTRACT

The subject guide catheter extension system with a micro-catheter delivery catheter includes an outer sheath, an inner member extending within the sheath, and a mechanism for engagement/disengagement of the inner member to/from the sheath. Several mechanisms of engagement/disengagement between the inner and outer members are provided including a friction mechanism, threaded mechanism, pull away sheath, and engagement/disengagement mechanism for pusher's handles. The sheath and the inner member are modified for different engagement/disengagement mechanisms operation. A micro-catheter delivery system provides for an improved atraumatic crossability to the treatment site in an expedited and simplified fashion. During a procedure, a guidewire along with a guide catheter are advanced to the vicinity of the treatment site within a blood vessel. Subsequent thereto, the subject guide catheter extension system is manipulated to advance the micro-catheter along the guidewire inside the guide catheter towards and beyond the site of interest. Once the micro-catheter is in place, the outer (Continued)

sheath slides along the micro-catheter until reaching the lesion, and then the inner member is removed from the sheath, and the sheath then is ready for passing the treatment catheter (stent/balloon) towards the lesion to be treated.

34 Claims, 17 Drawing Sheets

(51) Int. Cl.
 *A61M 25/01* (2006.01)
 *A61M 25/00* (2006.01)
(52) U.S. Cl.
 CPC ....... *A61M 25/104* (2013.01); *A61M 25/0054* (2013.01); *A61M 25/0068* (2013.01); *A61M 25/0102* (2013.01); *A61M 2025/0042* (2013.01); *A61M 2025/0183* (2013.01)
(58) Field of Classification Search
 CPC .......... A61M 25/09041; A61M 25/104; A61M 25/0054; A61M 25/0068; A61M 25/0108; A61M 25/0023; A61M 2025/0175; A61M 2025/0062; A61M 2025/0042; A61M 2025/0183; A61M 2025/0656; A61M 25/065; A61M 25/0606; A61M 25/0012; A61M 25/0136
 See application file for complete search history.

(56) References Cited

U.S. PATENT DOCUMENTS

| | | | |
|---|---|---|---|
| 5,234,416 A | 8/1993 | Macaulay et al. | |
| 5,704,926 A | 1/1998 | Sutton | |
| 5,813,405 A | 9/1998 | Montano, Jr. et al. | |
| 5,947,925 A | 9/1999 | Ashiya et al. | |
| 6,120,480 A * | 9/2000 | Zhang | A61M 25/0662 604/164.01 |
| 6,648,854 B1 | 11/2003 | Patterson et al. | |
| 7,993,351 B2 | 8/2011 | Worley et al. | |
| 8,048,032 B2 | 11/2011 | Root et al. | |
| 8,142,413 B2 | 3/2012 | Root et al. | |
| 8,292,850 B2 | 10/2012 | Root et al. | |
| 8,361,057 B2 | 1/2013 | Tanghoej et al. | |
| 8,365,087 B2 | 1/2013 | Glaser-Seidnitzer et al. | |
| 8,652,193 B2 | 2/2014 | Dorn | |
| 8,747,428 B2 | 6/2014 | Fischell et al. | |
| 8,821,485 B2 | 9/2014 | Herberer | |
| RE45,380 E | 2/2015 | Root et al. | |
| 8,996,095 B2 | 3/2015 | Anderson et al. | |
| 8,996,096 B2 | 3/2015 | Kinsley et al. | |
| RE45,760 E | 10/2015 | Root et al. | |
| RE45,776 E | 10/2015 | Root et al. | |
| RE46,116 E | 8/2016 | Root et al. | |
| 9,681,882 B2 * | 6/2017 | Garrison | A61M 1/008 |
| 9,687,634 B2 | 6/2017 | Grovender et al. | |
| 9,764,118 B2 | 9/2017 | Anderson et al. | |
| RE47,379 E | 5/2019 | Root et al. | |
| 10,449,339 B2 | 10/2019 | Wilson et al. | |
| 10,786,655 B2 * | 9/2020 | Lenker | A61M 25/09025 |
| 11,020,133 B2 | 6/2021 | Wilson et al. | |
| 2002/0087076 A1 * | 7/2002 | Meguro | A61M 25/0662 600/433 |
| 2003/0105451 A1 * | 6/2003 | Westlund | A61M 25/0021 604/532 |
| 2005/0273074 A1 | 12/2005 | Lewis | |
| 2008/0183128 A1 * | 7/2008 | Morriss | A61M 3/0283 604/35 |
| 2008/0281228 A1 * | 11/2008 | Parodi | A61M 25/09 600/585 |
| 2009/0018525 A1 | 1/2009 | Waite et al. | |
| 2009/0082800 A1 | 3/2009 | Janardhan | |
| 2009/0156953 A1 | 6/2009 | Wondka et al. | |
| 2010/0305475 A1 | 12/2010 | Hinchliffe et al. | |
| 2011/0054503 A1 | 3/2011 | Rizk et al. | |
| 2011/0112567 A1 | 5/2011 | Lenker et al. | |
| 2011/0301502 A1 | 12/2011 | Gill | |
| 2013/0116701 A1 | 5/2013 | Wang et al. | |
| 2013/0237962 A1 * | 9/2013 | Kawai | A61M 25/0102 604/524 |
| 2014/0012281 A1 * | 1/2014 | Wang | A61M 25/0023 606/108 |
| 2014/0018773 A1 | 1/2014 | Wang et al. | |
| 2014/0058251 A1 * | 2/2014 | Stigall | A61B 5/1076 600/424 |
| 2014/0194918 A1 | 7/2014 | Tegels | |
| 2014/0236088 A1 | 8/2014 | Al-Rashdan et al. | |
| 2014/0276618 A1 * | 9/2014 | Di Caprio | A61M 25/0068 604/510 |
| 2015/0005801 A1 * | 1/2015 | Marquis | A61M 25/0097 606/194 |
| 2015/0151090 A1 | 6/2015 | Sutton et al. | |
| 2015/0173782 A1 | 6/2015 | Garrison et al. | |
| 2015/0265806 A1 * | 9/2015 | Kawaguchi | A61M 25/0097 604/539 |
| 2016/0121080 A1 | 5/2016 | Cottone | |
| 2016/0144155 A1 | 5/2016 | Simpson et al. | |
| 2016/0249942 A1 * | 9/2016 | Olson | A61B 17/22 604/509 |
| 2016/0346506 A1 * | 12/2016 | Jackson | B29C 63/00 |
| 2017/0028170 A1 | 2/2017 | Ho | |
| 2018/0008801 A1 | 1/2018 | Solar et al. | |
| 2018/0126121 A1 * | 5/2018 | Mauch | A61M 25/0043 |
| 2018/0193042 A1 * | 7/2018 | Wilson | A61B 17/22 |
| 2019/0255299 A1 | 8/2019 | Fischell et al. | |
| 2020/0179661 A1 | 6/2020 | Fischell et al. | |

OTHER PUBLICATIONS

International Search Report and Written Opinion of International Searching Authority (US) Regarding Corresponding Application PCT/US2019/012678, dated Mar. 25, 2019.
International Search Report and Written Opinion of PCT Application No. PCT/US2020/057064, dated Jan. 25, 2021; 26 pages.
U.S. Appl. No. 16/184,706 filed Nov. 8, 2018, Root et al.
U.S. Appl. No. 16/220,925 filed Nov. 12, 2018, Root et al.
U.S. Appl. No. 16/220,951 filed Dec. 14, 2018, Root et al.
U.S. Appl. No. 16/220,975 filed Dec. 14, 2018, Root et al.
U.S. Appl. No. 16/220,996 filed Dec. 14, 2018, Root et al.

* cited by examiner

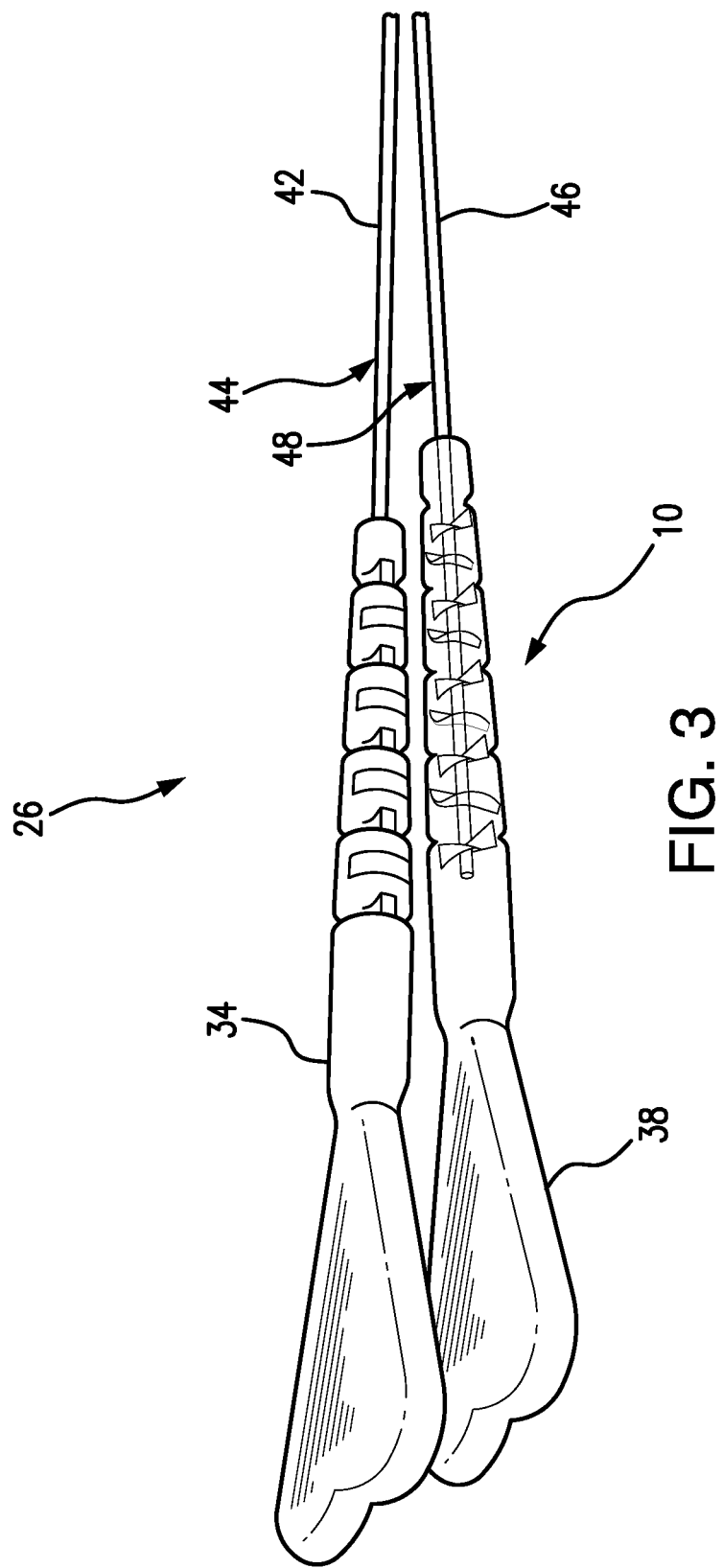

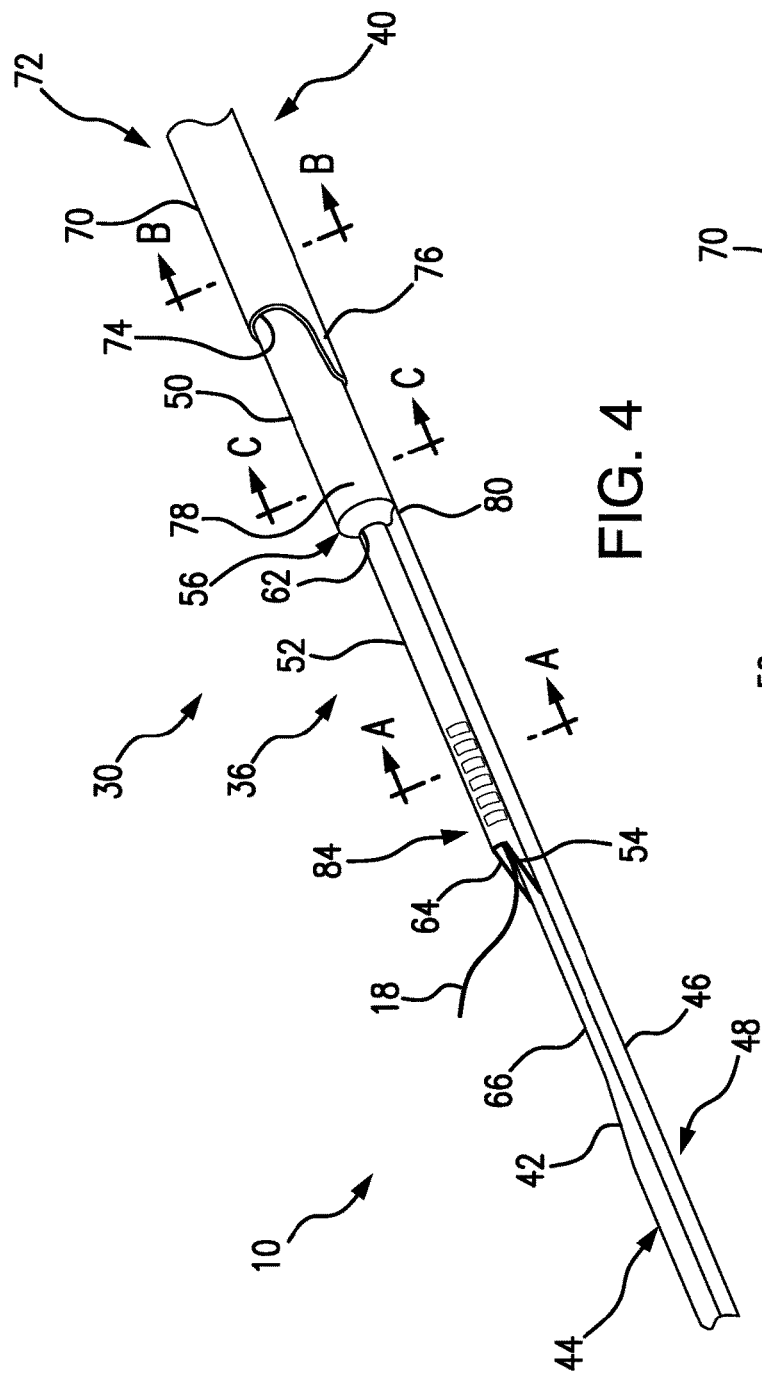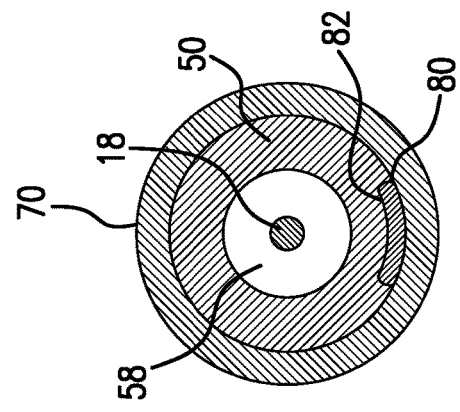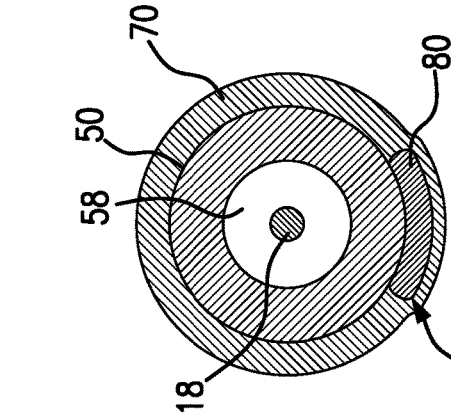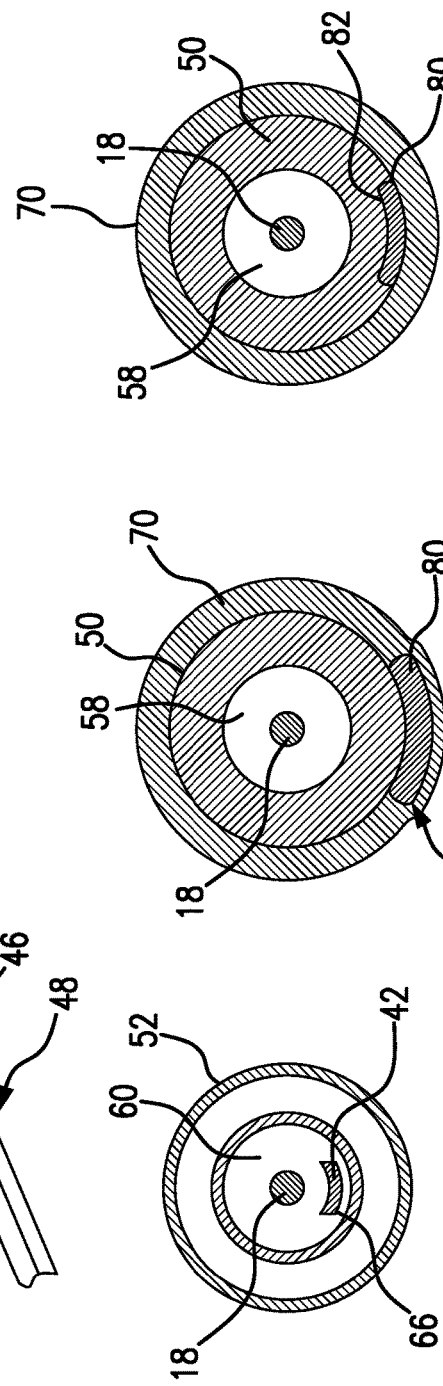

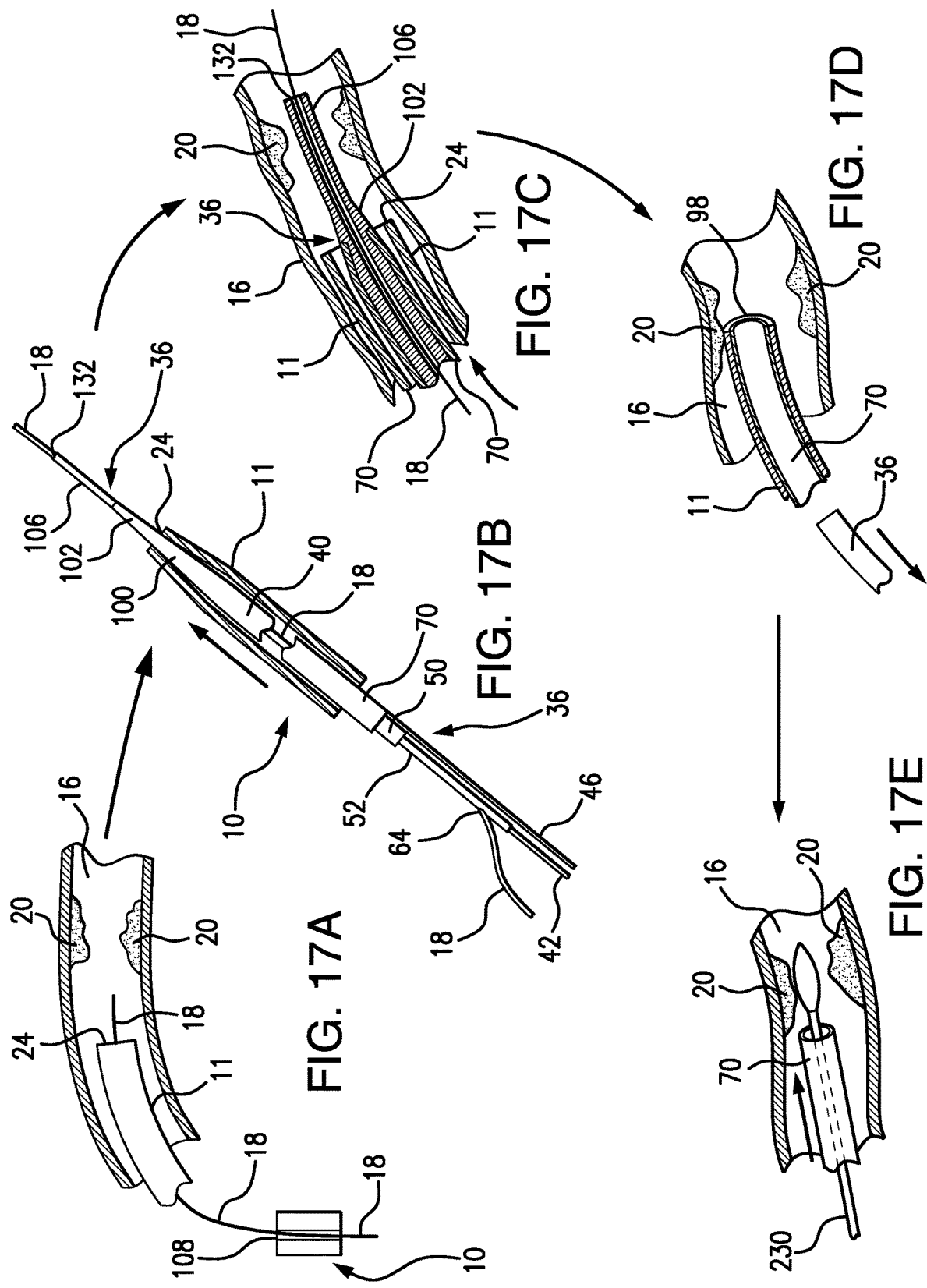

GUIDE CATHETER EXTENSION SYSTEM WITH A DELIVERY MICRO-CATHETER CONFIGURED TO FACILITATE PERCUTANEOUS CORONARY INTERVENTION

FIELD OF THE INVENTION

The present invention is directed to medical devices, and particularly, to minimally invasive devices used for treatments within the human vasculature, such as, for example, coronary arteries.

The present invention is further directed to devices designed for atraumatic, fast, simple delivery and replacement of catheters in coronary arteries or other blood vessels in the human body to facilitate percutaneous revascularization.

The present invention is also directed to medical devices for intravascular procedures using a guide catheter extension system equipped with a delivery micro-catheter that permits easy delivery of the distal portion of the tubular guide extension system to, and beyond, a lesion to be stented (treated).

The present invention further is directed to a medical device that includes a thin-walled tubular guide catheter extension system that is delivered co-axially to, and/or beyond, a coronary artery obstruction lesion by virtue of an integrated micro-catheter system to allow the distal delivery of the guide extension device with minimal trauma while passing through a coronary artery.

The present invention is also directed to a guide catheter extension system operating with a co-axial highly flexible tapered delivery micro-catheter positioned at the distal end and fitted within of the catheter extension system specifically designed to track over a guidewire and configured to deliver the guide extension distal end to, and beyond, a lesion of interest. The guide catheter extension system has a miniature profile (at its distal end) with a diameter less than 1 mm, and equipped with a lubricity coating to permit the distal tip to attain the "crossability" that would be superior to that of the distal tip of a conventional balloon angioplasty catheter, and far superior to the distal tubular end of a conventional guide extension device.

Additionally, the present invention is directed to an intravascular guide catheter extension system using an inner member reciprocable internally of an outer member (a sheath), and configured with a tapered micro-catheter at its distal end. A connection sub-system is provided which controllably connects/disconnects (engages/disengages) the inner and outer member for joined motion within a guiding catheter, or relative displacement of the inner and outer member each with respect to another as required by the intravascular procedure.

BACKGROUND OF THE INVENTION

Coronary artery obstruction disease, or a disease in the peripheral vasculature, is often treated by the balloon angioplasty and/or stent placement. The advancement of the revascularization devices, such as balloons or stent delivery systems, within the blood vessels to a treatment site can be challenging in case of tortuosity and/or calcification of the vessels.

Revascularization devices usually use guiding (or guide) catheters for delivery of such devices to the site of treatment. The use of guide catheters alone to "back up" the advancement of the revascularization devices to the coronary arteries may be limited and challenging.

In order to facilitate the revascularization devices delivery to the site of interest, guide catheter extension systems have been designed and used during cardiac procedures.

For example, the guide extension system, such as "Guideliner™," is produced by Vascular Solutions. This guide extension system is described in U.S. Pat. No. 8,292,850, authored by Root, et al. Root, et al. (U.S. Pat. No. 8,292,850) describes a coaxial guide catheter to be passed through a lumen of a guide catheter, for use with interventional cardiology devices that are insertable into a branch artery that branches off from a main artery.

The Root coaxial guide catheter is extended through the lumen of the guide catheter and beyond its distal end and inserted into the branch artery. Root uses the guide extension supported by a tapered inner catheter. The purpose of the inner catheter is to provide an atraumatic tip to avoid vessel injury, while advancing the guide extension into the proximal portion of a coronary vessel.

Another guide extension system, such as "Guidezilla™", has been designed and manufactured by Boston Scientific. This guide extension system is described in U.S. Pat. No. 9,764,118, authored by Anderson, et al. Anderson's guide extension system uses a push member having a proximal portion having a proximal stiffness, a distal portion having a distal stiffness different from the proximal stiffness, and a transition portion disposed and providing a smooth transition between the proximal and distal portions. A distal tubular member is attached to the push member and has an outer diameter larger than the outer diameter of the push member.

U.S. Patent Application Publication #2017/0028178, authored by Ho, describes a guide extension system using a slit catheter which is extendable upon insertion of a balloon or stent delivery system. Ho's guide extension also uses a rigid push rod to assist in delivery of the guide extension to the treatment site.

The systems, "Guideliner™" and "Guidezilla™", as well as the Ho's system, support the concept of advancing the guide extension system through the guiding catheter, and partially down the coronary artery, in order to achieve additional "back up" support to deliver balloon dilatation catheters and/or stent delivery catheters to the site of intended treatment.

The function of these guide extensions are to permit closer approach to the lesion to provide additional support in crossing the lesion to be treated with an interventional device. However, despite the additional support, the lesion to be treated can still be difficult or nearly impossible to pass through with a stent delivery system, due to fibrosis, calcification, and/or angulation at the lesion site.

One of the limitations of the currently used guide extension devices is that they use a relatively blunt and large caliber cylindrical distal end. Relatively high profile distal edges have a limited deliverability of the guide extension in many cases, and permit the advancement only to the proximal or mid portion of the coronary artery to be treated. Very rarely, if ever, can the guide extension be delivered to the actual lesion to be treated with angioplasty or stenting, even after balloon pre-dilatation of the lesion.

U.S. Patent Application Publication #2011/0301502, authored by Gill, describes a catheter with a longitudinal separation, allowing for the positioning device to be smaller in diameter than the stent delivery system. The Gill device, however, does not envision an inner catheter to permit easy and atraumatic crossing of the lesion to be treated. The Gill system acts merely as a covering for the stent delivery system, which can be removed after advancement of the stent delivery system, due to the longitudinal separation.

Thus, a device and method that would permit a delivery of the distal portion of the tubular guide extension system to, or ideally, beyond, the lesion to be treated, would have significant advantages over conventional guide extension devices, such as the "Guideliner" (Vascular Solutions), or the "Guidezilla" (Boston Scientific), and others.

It would be highly desirable to provide a guide extension system which can be delivered to the vessel and just beyond the actual lesion, and which would be able to act as a sheathing system to allow rapid delivery of the even long, relatively high profile stent delivery systems to the target lesion.

It would also be highly desirable to provide a placement of catheters into coronary arteries, or other arteries in human body in order to facilitate percutaneous revascularization procedures by using a tapered micro-catheter fitted within the guide extension system to guide the extension distal end to, and past, the lesion to be treated. This would represent substantial improvement upon conventional guide extension systems and which would overcome limitations of such systems.

Although a concept of a tapered piece inside a guide extension catheter is envisioned by Root, this system uses a very short taper, and does not envision the taper as a longer integrated member of the whole system, nor does it envision that this inner piece would travel coaxially over a guidewire. Nor does Root describe, anticipate or envision a longer system delivery system, with a very low profile tip which would be beneficial in attaining the coaxial delivery of the guide extension past a lesion of interest. Such an embodiment has never been commercialized, and the description of the tapered tip inner device was only meant as a means for the proximal delivery of the blunt tip of the guide catheter extension out of the guiding catheter.

SUMMARY OF THE INVENTION

It is therefore an object of the present invention to provide a medical device for intravascular application that attains delivery of a minimally traumatic thin-walled tubular guide catheter extension system to, and beyond, a coronary artery obstructive lesion by virtue of an integrated micro-catheter system.

It is another object of the present invention to provide a guide catheter extension system using a coaxial, highly flexible, and removable delivery micro-catheter which is specifically configured to track over a 0.009-0.014" guidewire, which has a diameter at its distal tip of less than 1.0 mm, and is improved with a lubricity coating which permits the "crossability" of the distal tip that is superior to that of a conventional balloon angioplasty catheter.

One of the objects of the subject invention is to use a highly flexible tapered elongated micro-catheter delivery catheter to deliver the distal tip of a guide extension "sheath" to, and beyond, a target lesion to be treated with angioplasty or stenting in a diseased human coronary artery.

It is an additional object of the present invention to provide a guide catheter extension system in which the total length of the tapered micro-catheter delivery system can extend over 1.5 cm (ideally 2-4 cm) beyond the distal tip of the tubular guide extension system, and which can be movably exchanged within the guide extension system ("sheath") to allow removal of the micro-catheter delivery piece and exchange for a balloon angioplasty or a stent delivery catheter over the same guidewire that was used to deliver the micro-catheter and guide extension system, which allows easy passage to, and beyond, a lesion of interest in a diseased human coronary artery.

It is a further object of the present invention to provide a guide catheter extension system in which an outer member built with a stent delivery catheter "sheath" is guided over a micro-catheter to be advanced over the micro-catheter delivery catheter beyond a lesion of interest to be treated with balloon angioplasty or stenting. Once the guide extension tip of the catheter "sheath" is advanced over the tapered guide extension micro-catheter delivery catheter to a distal position, a rapid exchange, or alternatively, an over-the-wire inner member (micro-catheter delivery device) is removed, while the 0.014" coronary guidewire is left in place in the more distal portion of the target vessel, and a treatment catheter may be advanced inside of the "sheath" to the treatment site.

It is an additional object of the present invention to provide a guide extension system configured with the stent delivery catheter "sheath" deliverable to the treatment site inside a vascular structure in an atraumatic manner to attain easy passage of the stent system therethrough. This expedites the cardiac procedure and permits percutaneous coronary intervention to be performed with less radiation dose and with virtually no risk of stent embolization from the stent delivery system.

It is a further object of the present invention to provide a guide catheter extension system in which the tubular sheath of the guide catheter extension system may be formed from or reinforced with a flat wire helical coil (with a wire thickness of approximately 1 mil to 3 mils). Such flat wire helical coil is either embedded in the plastic wall of the sheath, or has a very thin coating of plastic placed onto its inner and outer surfaces. This design reduces the wall thickness of the tubular sheath of the guide extension system to less than 7 mils, and, preferably, to around 5 mils. The micro-catheter at the distal end of the inner member is also envisioned as being formed from or reinforced with the flat wire helical coil, which may have a pitch changing along the micro-catheter length to provide a flexibility gradient beneficial for operation and atraumatic qualities of the subject system. Such a novel construction reduces the outside diameter of the subject guide catheter extension compared to existing guide extension systems.

Furthermore, it is an object of the present invention to provide a guide extension system having a shaft which employs a thin-walled, flat wire helical coil fabricated from a shape memory alloy such as Nitinol to prevent the possibility of kinking of the tubular shaft of the guide extension catheter.

Still another object of the invention is to provide a micro-catheter delivery system that has a balloon on its proximal portion to permit balloon expansion, after it has been advanced into the coronary artery and to an area of interest.

Still another object of the invention is to provide an outer member/sheath whose distal end is tapered, and can be stretched during the withdrawal of the inner member, thus allowing a nearly flush outer surface at the point at which the inner member exits the outer member.

In one aspect, the present invention constitutes an intravascular system equipped with a guide catheter extension sub-system cooperating with a guide wire removably advanceable in a blood vessel of interest to or beyond a treatment site and displaceable internally of a guide catheter.

The guide catheter extension sub-system is configured for controllable displacement along the guide wire. The guide catheter extension sub-system has a proximal portion, a distal portion, and a middle junction portion interconnected between the proximal and distal portions of the guide catheter extension sub-system.

The guide catheter extension sub-system comprises:

(a) an outer member formed by a substantially cylindrically contoured elongated flexible sheath defining a sheath lumen having a proximal end and a distal end. The sheath extends between the middle junction and distal portions of the guide catheter extension sub-system;

(b) an inner member having an elongated body defining an internal channel extending along the longitudinal axis thereof. The inner member extends internally along the sheath lumen in a controllably displaceable relationship with the sheath. The inner member has a distal end configured with a tapered delivery micro-catheter having an elongated body of a predetermined length (preferably, exceeding 2 cm). The tapered delivery micro-catheter is displaceable along the guide wire beyond the distal end of the sheath; and (c) an interconnection mechanism disposed in an operative coupling with the inner and outer members of the guide catheter extension sub-system and controllably actuated to operate the guide catheter extension sub-system in an engaged or disengaged modes of operation.

In the engaged mode of operation, the inner and outer members of the guide catheter extension sub-system are engaged for a controllable common displacement along the guide wire, and in the disengaged mode of operation, the inner and outer members are disengaged for a controllable individual linear or rotational displacement relative one another.

Preferably, the micro-catheter is formed of a flexible material having differential flexibility along its length. The flexibility of the micro-catheter increases towards its distal end. In one embodiment, the micro-catheter is configured with a flat wire helical coil extending along the predetermined length of the micro-catheter. The pitch of the flat wire helical coil changes along the length of the micro-catheter to increase the flexibility of the micro-catheter towards its distal end.

It is of importance that the predetermined length of the micro-catheter exceeds 2 cm, and a diameter of the micro-catheter at its distal end does not exceed 1 mm.

The sheath, at its distal end, is configured with a tapered outer tip, and the inner member, at its distal end, is configured with a tapered distal tip. The tapered distal tip of the inner member interfaces, at its outer surface, with an inner surface of the tapered outer tip of the sheath. It is of a paramount importance that a dimensional transition between the outer diameter of the outer tip of the sheath and the outer diameter of the distal tip of the inner member does not exceed 0.006" in order to form a substantially flush transition therebetween and provide a smooth outer surface at the distal portion of the subject guide catheter extension sub-system.

The subject guide catheter extension sub-system further comprises an inner member pusher which is coupled, at its distal end, to a proximal end of the inner member, and an outer member pusher which is coupled, at its distal end, to the proximal end of the outer member. The inner and outer member pushers are actuated by a surgeon (operator) to control the displacement of the inner and outer member along the guide wire, as well as a linear and/or rotational displacement of the inner and outer members relative one another.

The guide catheter extension sub-system further includes an inner member pusher handle, and an outer member pusher handle. The inner member pusher is attached, at its proximal end, to the inner member pusher handle, and the outer member pusher is attached, at its proximal end, to the outer member pusher handle.

The interconnection mechanism in the subject guide catheter extension sub-system is envisioned in a number of alternative embodiments. For example, in one embodiment, the interconnection mechanism is operatively coupled to the inner and outer member pusher handles, and includes tabs extending at opposite sides of one of the inner and outer member pusher handles, and notches formed at respective sides of another one of the inner and outer member pusher handles. The tabs disengageably cooperate with the notches, thus forming a snap-based interconnection mechanism.

In an alternative embodiment, the interconnection mechanism is a friction-based mechanism created between an outer surface of the inner member and an inner surface of the sheath of the outer member at at least one area along their interfacing length.

In yet another embodiment, the interconnection mechanism is configured as a threaded engagement/disengagement mechanism which includes at least one engagement button extending above an external surface of the inner member, and at least one engagement slot configured at least at the proximal end of the sheath of the outer member. The engagement button is removably engaged (by operating the inner and/or outer member pushers) in the engagement slot in the engaged mode of operation for locking the inner and outer member one to another.

In a further alternative embodiment, the subject interconnection mechanism includes:

(a) a pull-away sheath formed with a substantially cylindrically shaped body having a wall defining an internal channel for receiving the inner and outer member pushers therein in the engaged mode of operation. The wall is pre-treated at predetermined areas for collapsing therealong; and (b) a cord in operative coupling, at one end thereof, with the wall. In the disengaged mode of operation, the cord is pullable to collapse the wall, thus disengaging the inner member pusher from the outer member pusher, for unlocking the inner member from the outer member.

Preferably, the subject guide catheter extension sub-system is configured with a flat wire helical coil member forming at least a portion of respective walls of the sheath and/or the micro-catheter.

The inner member includes, at its proximal end, a tubular member having a proximal opening formed in the tubular member's wall and an internal channel aligned with the inner channel of the inner member. The tubular member of the inner member may include a reinforced portion formed with a flat wire helical coil embedded in its wall and extended circumferentially around the internal channel of the tubular member.

In one implementation of the subject guide catheter extension sub-system, where the inner and outer member pushers are formed as solid wires with tapered distal ends, the guide wire and the tapered distal end of the inner member pusher are received in the internal channel of the tubular member through the proximal opening for extending along the internal channel of the tubular member substantially in parallel relationship.

The distal end of the outer member pusher preferably has a tapered arcuated configuration cooperating with a contour of the inner member at its proximal end. The distal end of the outer member pusher is fixedly attached to the proximal end of the sheath.

The flat wire helical coil which may be embedded in the wall of the tubular member, as well as in the walls of the sheath and/or micro-catheter, is formed of a radio-opaque material, preferably including a shape memory alloy, such as Nitinol.

It is envisioned that radio-opaque markers are attached to the distal ends of the sheath and the micro-catheter to facilitate a surgeon in performing the cardiac procedure.

In another alternative embodiment, the inner member pusher is formed in a tubular configuration having an internal channel extending along the longitudinal axis of the inner member pusher. In this embodiment, the inner member pusher handle includes an entrance channel communicating with the internal channel of the inner member pusher, and the guide wire enters into the internal channel of the inner member at its proximal end through the entrance channel of the inner member pusher handle in communication with the internal channel of the inner member pusher.

In another aspect, the present invention constitutes a method for intravascular treatment using a guide catheter extension system in cooperation with a guide wire and guide catheter. The subject method comprises the following steps:
(a) assembling a guide catheter extension system having:
an outer member formed by a flexible substantially cylindrically contoured elongated sheath defining a sheath lumen having a proximal end and a distal end,
an inner member having an elongated body defining an internal channel extending along its longitudinal axis. The inner member has a distal end configured with a tapered delivery micro-catheter having an elongated body of a predetermined length (preferably, longer than 2-3 cm). The inner member is extended in the sheath lumen in a controllably displaceable relationship with the sheath, and
an interconnection mechanism disposed in an operative coupling with the inner and outer members of the guide catheter extension system and controllably actuated (by a surgeon) to operate the guide catheter extension system in an engaged or disengaged modes of operation.

In the engaged mode of operation, the inner and outer members of the guide catheter extension system are engaged for a controllable common displacement along the guide wire and inside the guide catheter, and in the disengaged mode of operation, the inner and outer members are disengaged for a controllable individual linear and/or rotational displacement relative to one another, as well as for switching between the engaged and disengaged modes of operation.

The method further includes the following steps:
(b) upon assembling the guide catheter extension system, extending a guide wire along the internal channel of the inner member with a proximal end of the guide wire extending beyond a proximal end of the internal body, and a distal end of the guide wire extending beyond a distal end of the delivery micro-catheter;
(c) advancing the distal end of the guide wire into a blood vessel of interest towards a treatment site;
(d) controlling the interconnection mechanism to establish the engaged mode of operation;
(e) advancing the guide catheter extension system, in the engaged operational mode, within the guide catheter and along the blood vessel of interest with the micro-catheter sliding along the guide wire towards the treatment site until the micro-catheter is brought at least in alignment with or beyond the treatment site.

The subject method further advances to:
(f) controlling the interconnection mechanism to switch to the disengaged mode of operation to disengage the inner and outer members one from another; and
(g) subsequently thereto, advancing the sheath (remaining within the guide catheter) along the micro-catheter until the distal end of the sheath is brought in substantial alignment with the distal end of the micro-catheter and is brought in at least alignment or beyond the treatment site.

Subsequent to bringing the distal end of the sheath to a desired position, the subject method continues with the following procedures:
(h) removing the inner member from the sheath, yet leaving the sheath inside the blood vessel (within the guide catheter) with the distal end of the sheath in alignment with or beyond the treatment site; and
(i) advancing a treatment system (such as, for example, a balloon delivery system or a stent catheter) to or beyond the treatment site inside the sheath lumen for a required treatment of the blood vessel.

These and other objects and advantages of this invention will become obvious to a person of ordinary skill in this art upon reading the detailed description of the subject invention in conjunction with the patent drawings presented herein.

BRIEF DESCRIPTION OF THE DRAWINGS

FIG. 3 is representative of the proximal end of the subject system;

FIG. 4 is representative of a middle junction of the subject system with FIG. 4A being a cross-section of the tubular part in the inner member, taken along Lines A-A of FIG. 4, FIG. 4B being a cross-section of the interconnection unit taken along Lines B-B of FIG. 4, and, FIG. 4C being a cross-section of the interconnection unit taken along Lines C-C of FIG. 4;

FIGS. 17A-17E illustrate schematically a sequence of steps during the cardiac intervention procedure using the subject guide catheter extension system.

DETAILED DESCRIPTION OF THE PREFERRED EMBODIMENTS

Figure 1:
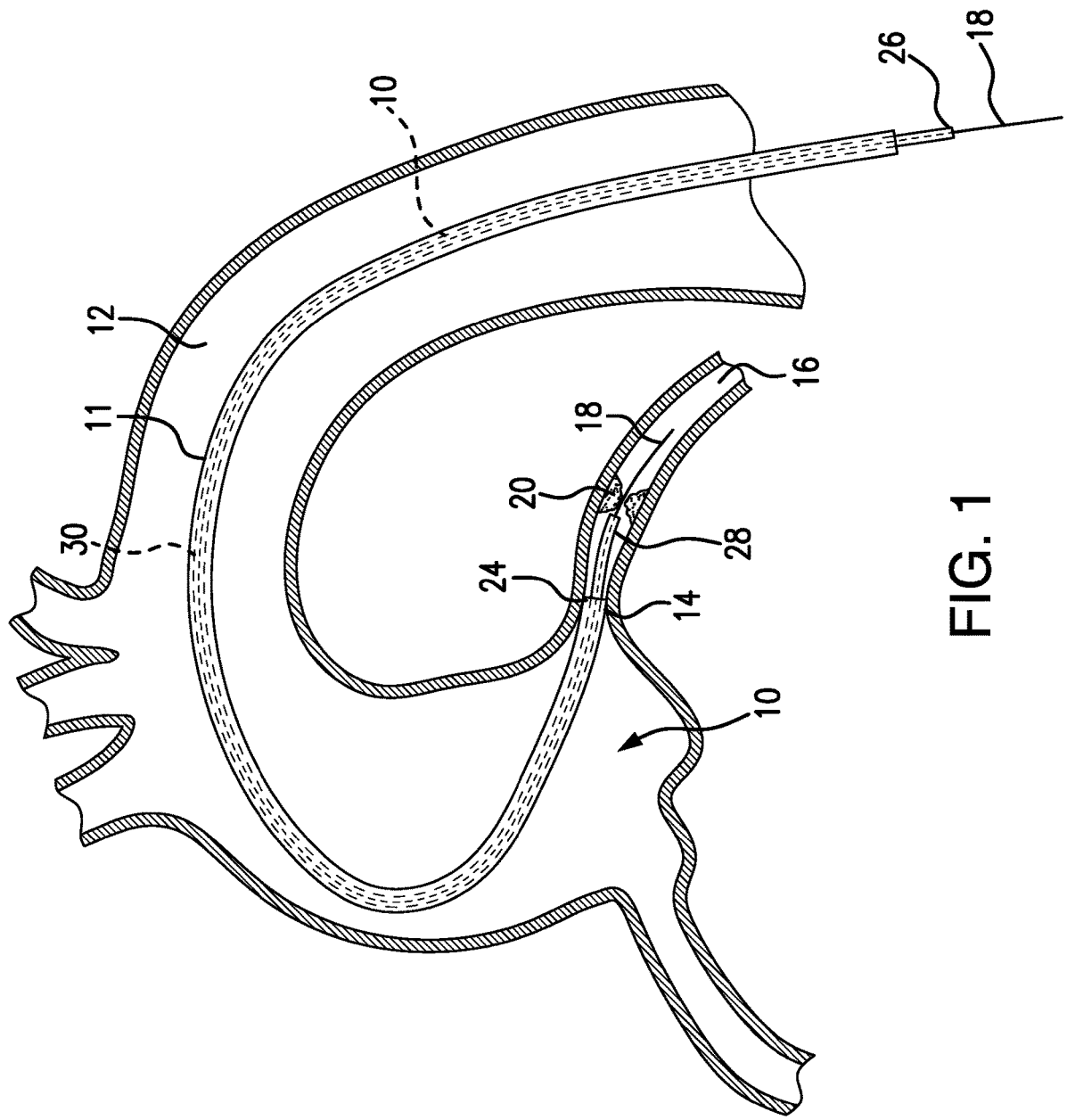
FIG. 1 shows schematically the subject guide catheter extension system advanced to the area of interest within a coronary artery.

FIG. 1 depicts a subject guide catheter extension system 10 which is used in conjunction with a guide catheter 11. At the initial stage of the procedure, the guide catheter 11 is advanced through a blood vessel 12 (such as the aorta) to a position adjacent to the ostium 14 of the coronary artery 16. A guidewire 18 is used during the cardiac procedure to guide the guide extension system 10 within the artery 16 toward a target location 20, as will be detailed in following paragraphs.

Subsequent to positioning of the distal end of the guide extension system 10 at the target location 20, a treatment system, such as a balloon catheter or stent system, may be advanced through the guide extension system 10 into the coronary artery 16 to the target location 20 to perform an intended cardiac treatment.

In order to reliably reach the target location, and even pass beyond the target location 20, the subject guide extension system 10 extends through the guide catheter 11 and beyond a distal end 24 of the guide catheter 11 deep into the coronary artery 16. The subject guide extension system 10, by extending beyond the distal end 24 of the guide catheter 11, provides an adequate reachability to the target location 20, and, by extending beyond the ostium 14 of the coronary artery 16, stabilizes the positioning of the guide catheter 11 and allows for an improved accessibility into the coronary artery 16 and to the target site 20.

Figure 2:
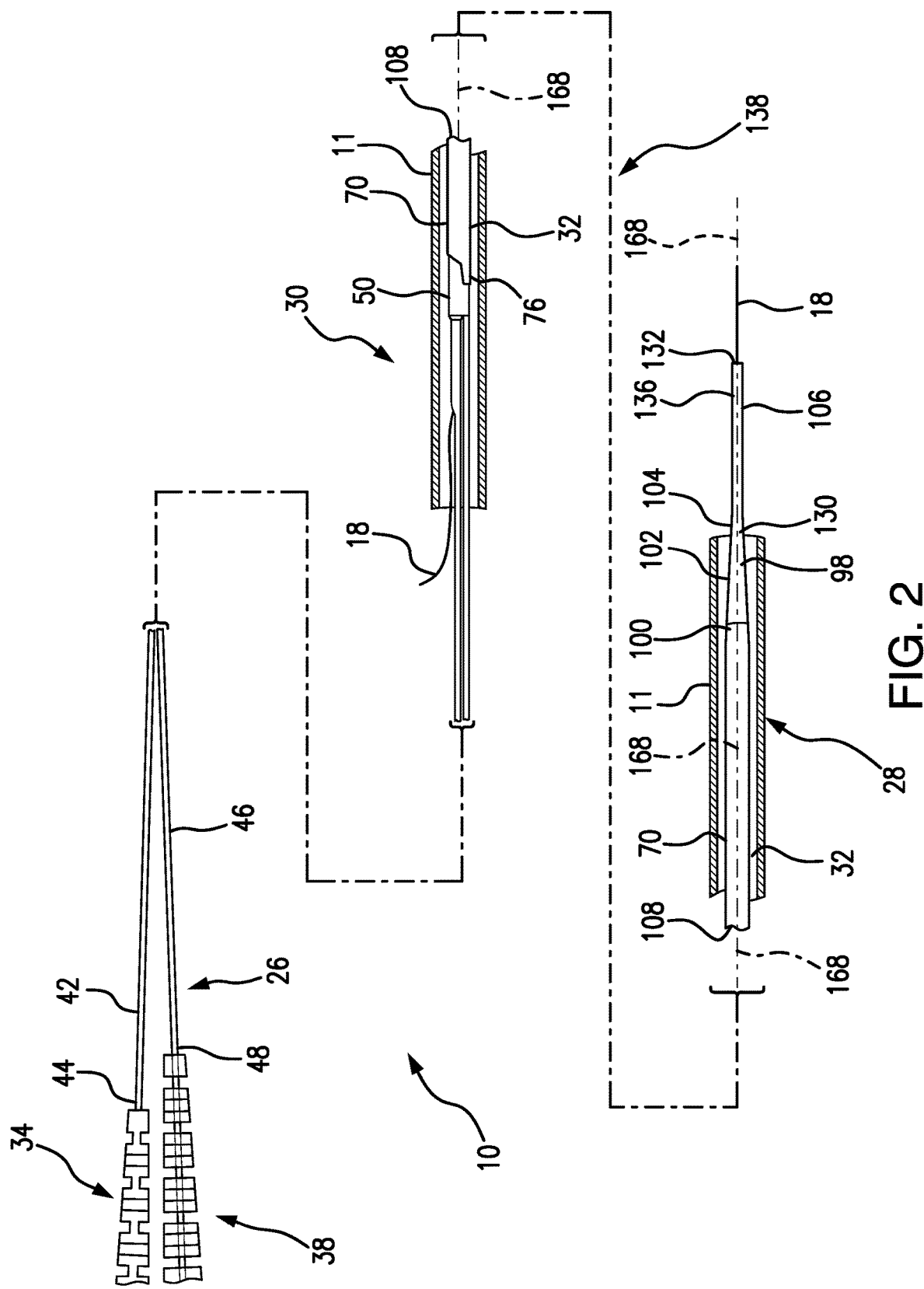
FIG. 2 shows schematically the subject guide catheter extension system.

As shown in FIG. 2, the subject guide extension system 10 includes a proximal end 26, a distal end 28, and a middle junction portion 30, interconnected between the proximal end 26 and the distal end 28 of the guide extension catheter system 10. The subject wire extension catheter system 10 is shown being extended within a lumen (internal channel) 32 of the guide catheter 11. The guide wire 18 is shown extending internally the guide extension system 10 along the longitudinal axis 168 thereof, and exits the system 10 beyond the outermost end 132 of the distal end 28 and between the proximal end 26 and the middle junction 30 in a manner detailed in further paragraphs.

Referring to FIGS. 2 and 3, the proximal end 26 of the subject guide extension system 10 is represented by a proximal handle 34 of an inner member 36 (to be detailed in further paragraphs) and a proximal handle 38 of an outer member 40 (to be detailed in following paragraphs).

An inner member pusher 42 is connected, at the proximal end 44 thereof, to the proximal handle 34 of the inner member 36. An outer member pusher 46 is connected, at the proximal end 48 thereof, to the proximal handle 38 of the outer member 40.

During the procedure, the proximal handle 34 of the inner member 36 and the proximal handle 38 of the outer member 40 are manipulated by a surgeon (operator) performing the coronary intervention procedure to position the guide extension catheter system 10 at the desired location 20, as well as to advance or retract the inner member 36 and the outer member 40 relative to the guide catheter 10 as required by the coronary intervention procedure.

Referring now to FIGS. 1, 2, 3, and 4, representative of one of the embodiments of the present guide extension catheter system 10, both inner and outer pushers 42 and 46 are made as solid wire members.

Referring to FIGS. 1, 2, 4, 4A-4C, and 5, the subject guide extension catheter system 10 includes the inner member 36 which is built, at the middle junction 30, with an interconnection unit 50 and a tubular part 52 connected, at the end 54 thereof, to a proximal end 56 of the interconnection unit 50. The interconnection unit 50 represents a cylindrically-shaped unit having, as shown in FIGS. 4B-4C, a lumen 58 formed therein along its longitudinal axis (which coincides with the longitudinal axis 168 of the guide catheter extension system 10).

As shown in FIGS. 4 and 4A-4C, the tubular part 52 is provided with a lumen 60 which is aligned, at the end 62 of the tubular part 52, with the lumen 58 at the proximal end 56 of the interconnection unit 50.

At the end 54 thereof, the tubular part 52 has an RX notch (Rapid Exchange Notch) 64 configured to receive the end 66 of the inner member pusher 42, as represented in FIG. 4A. Being received and extending through the lumen 60 of the tubular part 52, the end 66 of the inner member pusher 42 reaches the proximal end 56 of the interconnection unit 50 and is coupled (glued, welded, or otherwise fixedly attached) to the interconnection unit 50 to ensure that by manipulating the inner member pusher 42, a surgeon (operator) can control the positioning of the interconnection unit 50 (as well as the inner member 36 in its entirety).

The outer member 40 includes a "sheath" 70 made with a cylindrically shaped tubular body 72 extending substantially the entire length 138 of the subject system 10 and covering the middle junction 30 and the distal end 28 thereof. By manipulating the inner and/or outer member pusher(s) 42 and/or 46, a surgeon actuates a required linear and/or rotational displacement of the inner member 36 with regard to the "sheath" 70 of the outer member 40 (as will be detailed in further paragraphs), to advance or retract, the interconnection unit 50 to or from the guide catheter 11 by displacing the inner member 36 relative to the outer member 40, as required by the procedure performed.

Figure 9:
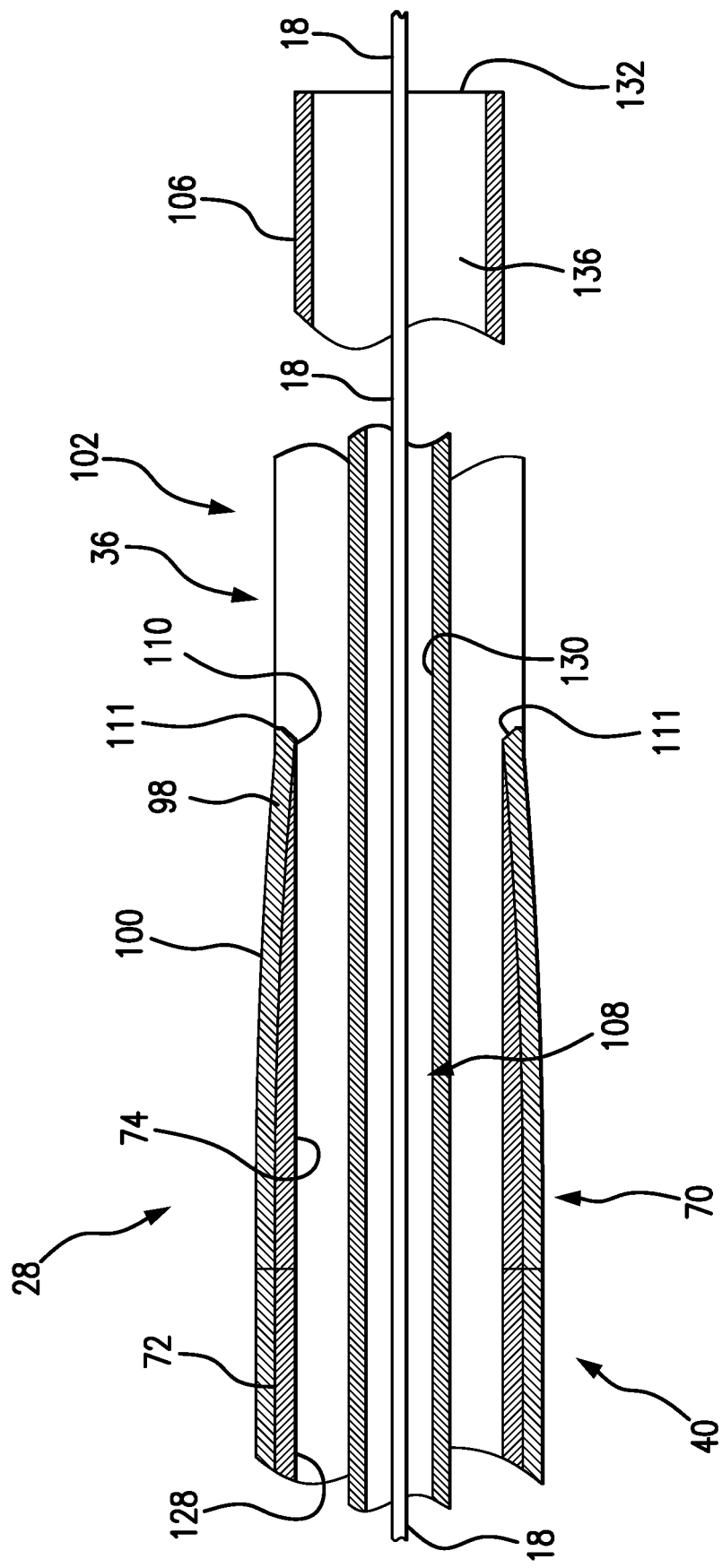
FIG. 9 shows the longitudinal cross-section of the distal end of the subject system.
Figure 10:
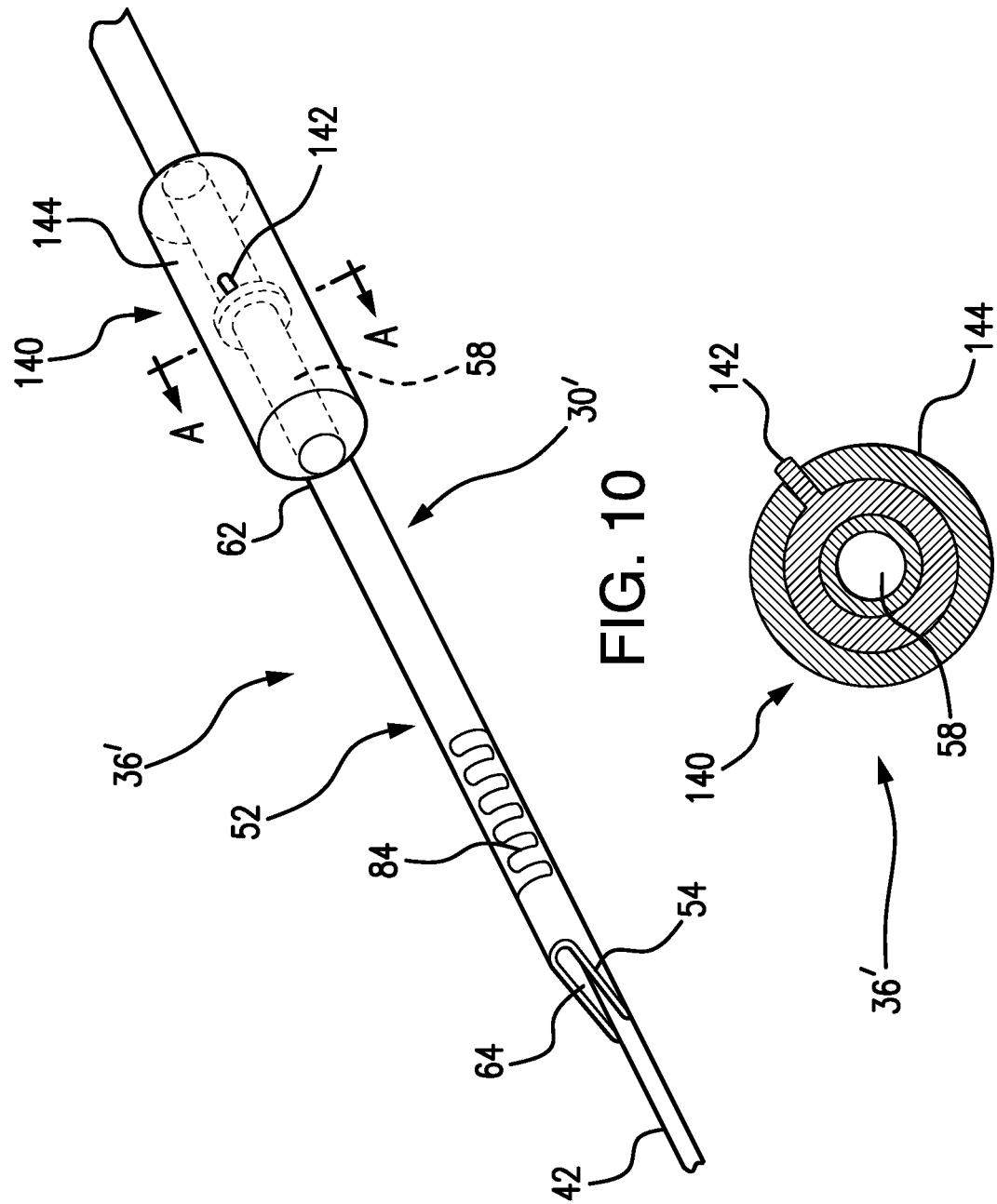
FIG. 10 depicts the middle junction of the subject system with an alternative engagement mechanism (between the inner and outer members), with FIG. 10A depicting a cross-section of the interconnection unit taken along Lines A-A of FIG. 10.

The guidewire 18 extends through the RX notch 54 of the tubular part 52 at the end 54 thereof and extends along the lumen 60 of the tubular part 52 in parallel with the inner member pusher 42 as shown in FIGS. 4 and 4A. The guidewire 18 also extends through the lumen 58 of the interconnection unit 50 (as depicted in FIGS. 4, and 4B-4C), and through the lumen 130 in the distal end 28 of the subject guide extension catheter system 10, as shown in FIG. 9, to be further described.

Figure 5:
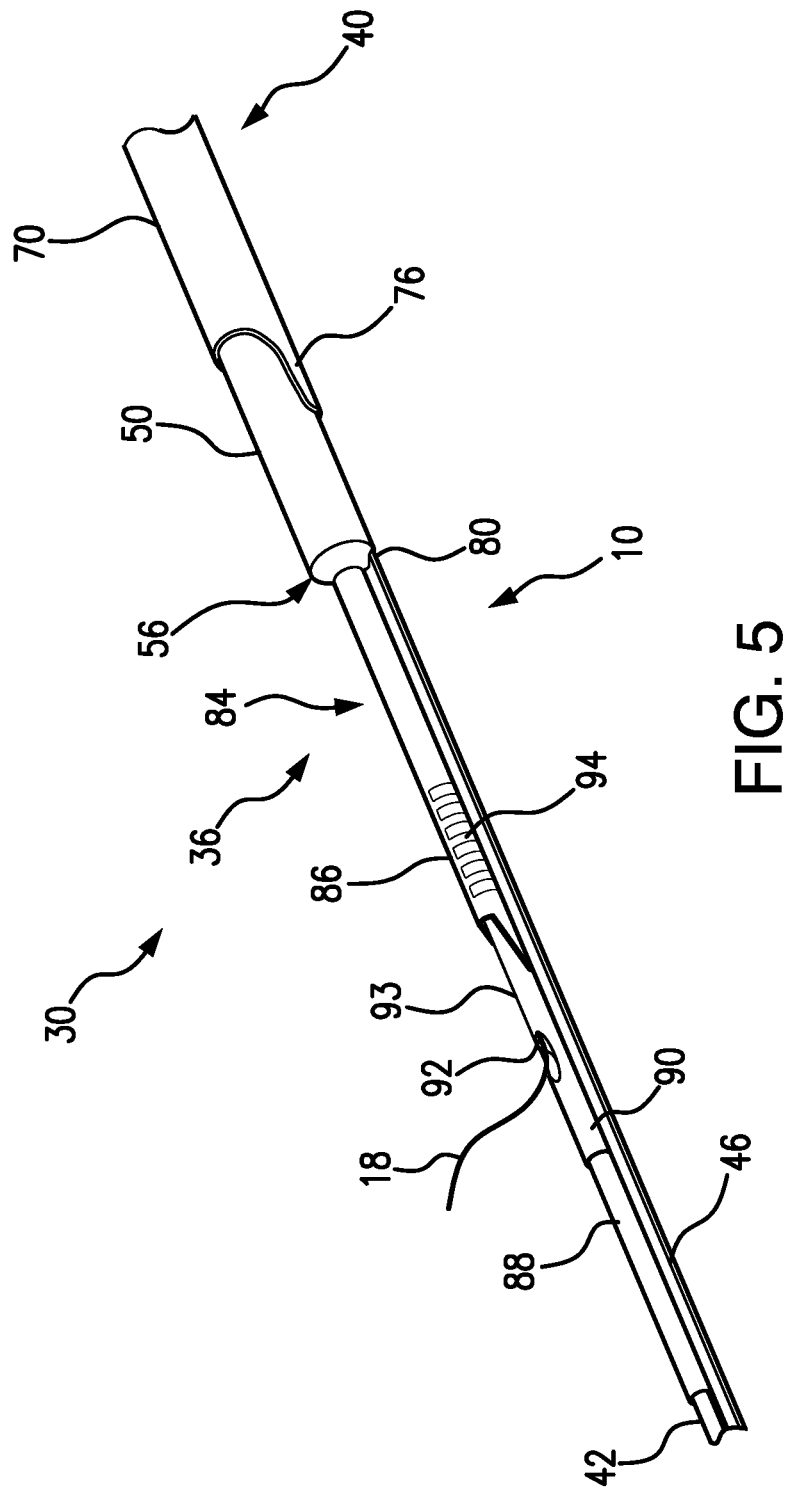
FIG. 5 depicts the middle junction of FIG. 3, detailing the brake reinforcement system.

As shown in FIGS. 4 and 5, illustrating the middle junction portion 30 of the subject guide extension catheter system 10, the outer member 40 is represented by the sheath 70 having the tubular body 72, the inner surface 74 of which, at its proximal end 76, interconnects with the outer surface 78 or the interconnection unit 50.

The subject guide catheter extension system 10 may operate in an inner/outer member engagement mode and in an inner/outer member disengagement mode.

There are several mechanisms envisioned in the subject guide extension catheter system 10 for controllable engagement/disengagement between the inner member 36 and the outer member 40, particularly, the sheath 70.

For example, as shown in FIGS. 4 and 5, in one of the embodiments, the interconnection unit 50 and the inner surface 74 of the sheath 70 are interconnected by a friction mechanism. The friction mechanism is used in the guide catheter extension system 10 to lock the inner member 36 and the outer member 40 together (when required by the cardiac procedure) to provide integral manipulation of the inner and outer members 36, 40, by actuating the inner and/or outer member pushers 42, 46, respectively, during the cardiac intervention procedure.

A similar friction-based engagement/disengagement mechanism may be provided at other locations along the length 138 of the inner/outer members interface, for example, at the distal end 28.

Alternative interconnecting mechanisms between inner and outer members 36, 40, will be presented in detail in following paragraphs.

Figure 6:
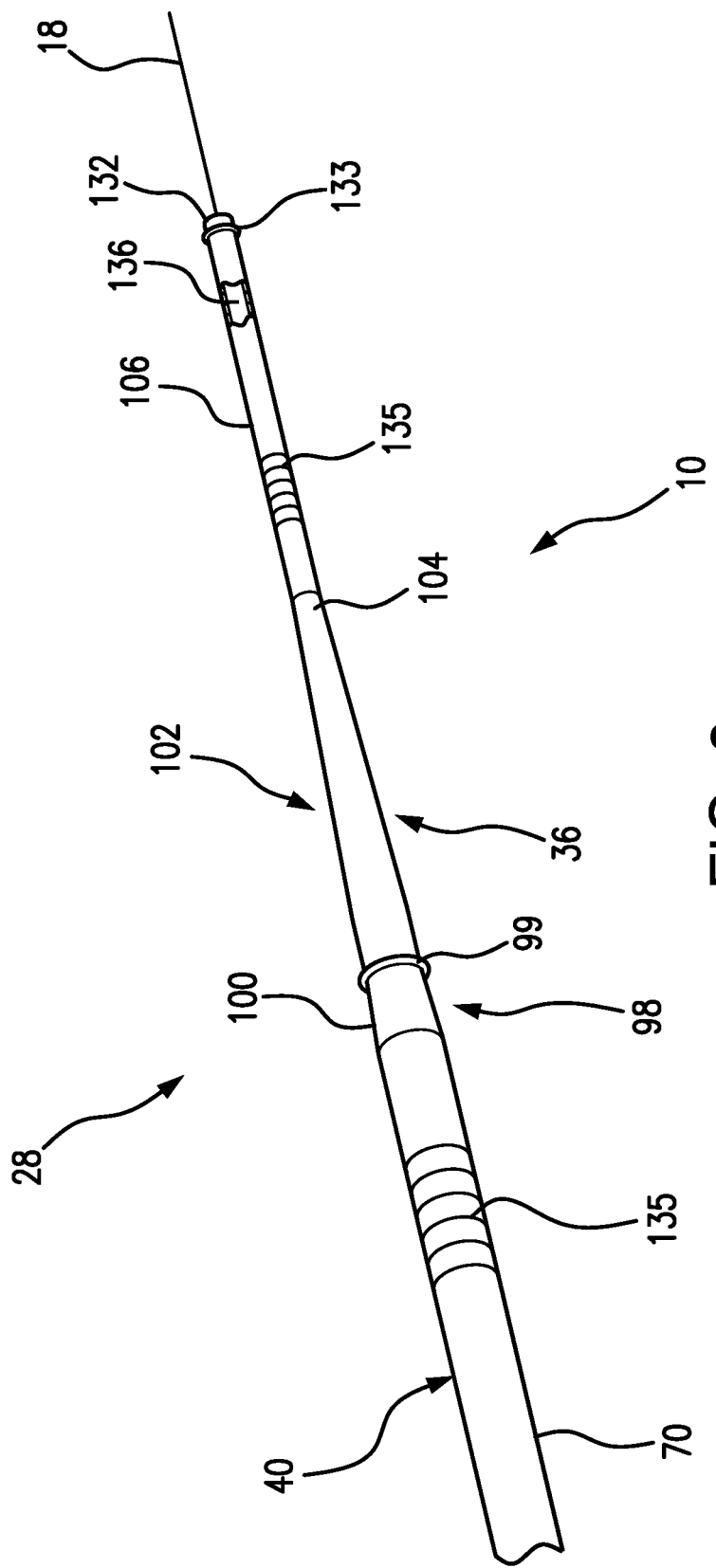
FIG. 6 depicts a distal end of the subject system.

The interconnecting mechanism may be controlled by a surgeon during the cardiac procedure to disengage the inner member 36 from the outer member 40 where a relative displacement of one with respect to another is required. Such disengagement of the inner and outer member is required during the cardiac procedure when the distal end 132 of the inner member 36 is to be advanced beyond the distal end 98 of the sheath 70 (as shown in FIGS. 6 and 17C), or when the inner member 36 is to be retracted from the sheath 70 and removed from the guide catheter 11 (as shown in FIG. 17D) prior to entering the balloon/stent catheter 230 to the lesion site 20 through the sheath 70 (as shown in FIG. 17E).

In order to provide enough room within the lumen 60 of the tubular part 52 for the guidewire 18, the inner member pusher 42 is somewhat tapered at its end 66, as shown in FIGS. 4 and 4A. Thus, the guide wire 18 has a sufficient room within the lumen 60 in the tubular part 52 to extend therealong.

The outer member pusher 46 is also tapered at its end 80, and is welded (glued, adhered, or otherwise fixedly attached) to the proximal end 76 of the tubular body 72 of the sheath 70. As shown in FIG. 4B, the tapered end 80 of the outer member pusher 46 may have a somewhat curved configuration in order to snugly cradle the portion of the outer surface 78 of the interconnection unit 50 in order to form a smooth surface at their interconnection, as well as to consume as little space within the sheath 70 as possible.

Referring to FIG. 5, the middle junction portion 30 of the subject guide extension catheter 10 may be manufactured with a braid reinforcement structure. The braid reinforcement member 84 includes a braid reinforced tube 86 that creates a somewhat flexible tubing connected to the interconnection unit 50 of the inner member 36, and a plastic tubing 88 that is connected to the proximal end 90 of the braid reinforced tubing 86 and bonded to the inner member pusher 42, as shown in FIG. 5.

The RX (rapid exchange) notch 92 for passing the guide wire 18 therethrough is formed through the wall 93 of the braid reinforced tubing 86. The braid reinforcement mechanism 84 may be configured with metallic patterns or wires within the braid reinforced tubing 86 to prevent kinking and which would give the braid reinforced tubing 86 a longitudinal stiffness. The metal braid portion 94 is embedded in the braid reinforced tubing 86 to add an increased flexibility thereto simultaneously with the stiffness required for advancing and retracting the inner member 36 relative to the sheath 70 during the procedure. A flat wire helical coil (made, for example, from a shape memory alloy, such as Nitinol) with a wire thickness of approximately 1 mil to 3 mils may be embedded in the braid portion 94. This coil may be formed with a very thin coating of plastic placed onto its inner and outer surfaces, which facilitates the reduction of the wall thickness of the tubing 86 to less than 7 mils and preferably to approximately 5 mils.

Figure 8:
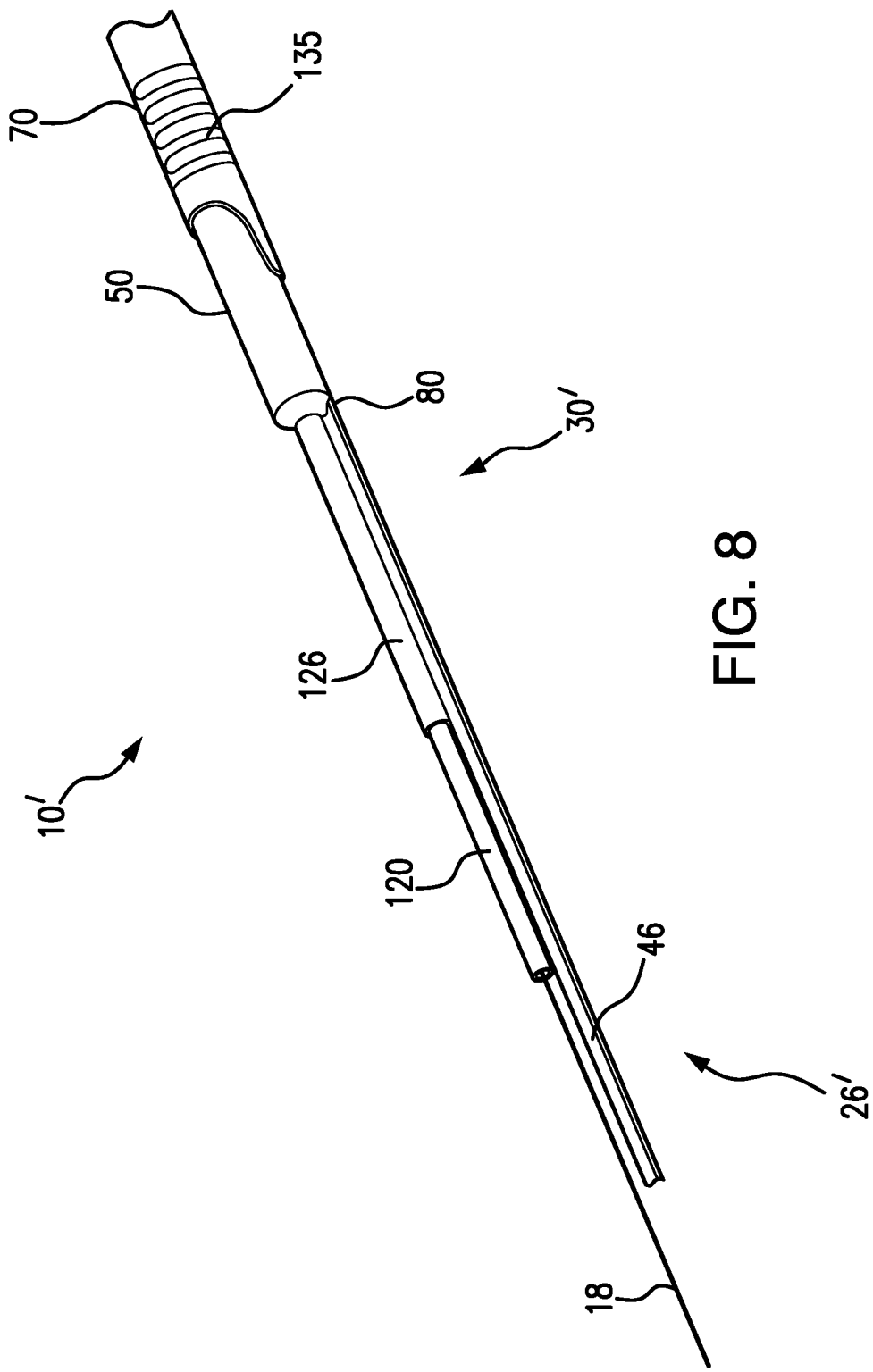
FIG. 8 details the middle junction of the subject system in its alternative embodiment.
Figure 11:
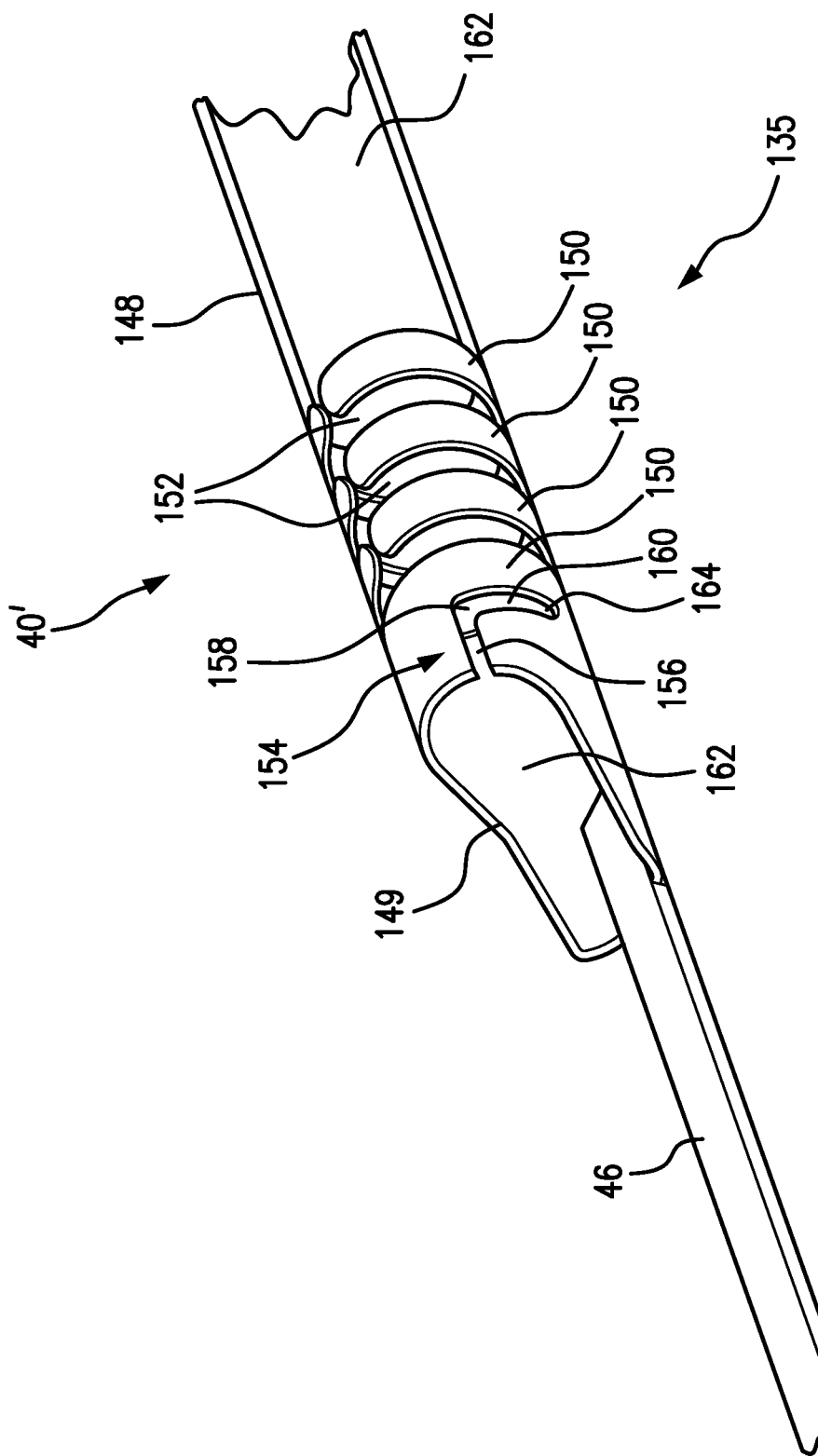
FIG. 11 shows the outer sub-assembly ("sheath") of the middle junction configured for cooperation with the inner sub-assembly of FIG. 10.

The principles of reinforcing tubular members by a flat wire helical coil or forming the tubular member from the flat wire helical coil may be applied in the subject guide catheter system 10 to the sheath 70, as well as to the micro-catheter 106. In the sheath 70 and/or the micro-catheter 106, such flat wire helical coil may be embedded in predetermined positions along the length of the walls thereof, for example, at the proximal and or distal ends. Alternatively, the entire length of the sheath 70 and/or micro-catheter 106 may be formed from the flat wire helical coil. The pitch between the coils may be changed to provide the flexibility gradient along the length of the tubular member (sheath 70 and or micro-catheter 106) increasing to the distal end thereof to facilitate atraumatic operation. The flat wire helical coil 135 is schematically depicted in FIGS. 6, 8, and 11. The length of the micro-catheter may exceed 2 cm.

Specifically, the subject guide catheter extension system 10 may be configured with a differential in micro-catheter flexibility with greater flexibility in the distal portion, by either changing the durometer of the plastic components from the "sheath's" proximal portion to its distal portion (i.e., higher durometer in the proximal rather than the distal portion), and/or changing the winding frequency (pitch) of the helical coil of wire in the micro-catheter 106 in the direction from the proximal portion to distal portion, such that the distal portion of the micro-catheter 106 is more flexible and trackable than the proximal portion of the micro-catheter delivery device, and has a substantially lower profile and more flexible than even the distal portion of the guide extension catheter ("sheath").

The system 10 could also include wires that have radio-opacity such that the guide extension system ("sheath") is easily visualized using fluoroscopy. It is also envisioned that both the tip 132 of the micro-catheter delivery portion 106 and the tip 98 of the sheath 70 will have one or more radio-opaque markers 99, 133 (shown schematically in FIG. 6) at or near the distal tip in order to permit an operator to distinguish between the two, which is particularly important as the obstructive lesion is crossed over with the micro-catheter, and the micro-catheter is held in place to allow the advancement of the tip of the "sheath" over the micro-catheter to the appropriate and ideal position, beyond, or in some cases just proximal, to the lesion to be treated.

As shown in FIGS. 2 and 6, the sheath 70 extends between its proximal end 76 at the middle junction 30 and its distal end 98 at the distal end 28 of the subject system 10 along the entire length 138 of the subject guide catheter extension system 10. As shown in FIG. 6, at the distal end 28 of the subject guide catheter extension system 10, the inner member 36 includes a distal tip 102 and a micro-catheter 106 (which may have a cylindrical configuration or a tapered cone-contoured configuration) formed integrally with the distal tip 102. At the distal end 98, the sheath 70 is formed with an outer tip 100 which may have a tapered cone-contoured configuration which may be frictionally (or through an alternative engagement/disengagement mechanism) interconnected with the distal tip 102 of the inner member 36.

As shown in FIGS. 2, 6, and 9, the distal tip 102 has a tapered configuration which changes gradually from the point of interconnection with the outer tip 100 of the sheath 70 to the distal end 104 of the distal tip 102. The micro-catheter 106 extends from the distal end 104 of the distal tip 102 of the inner member 36 in integral connection therewith and terminates in the distal end 132. The diameter of the micro-catheter 106 at the distal end 132 does not exceed 1 mm.

As shown in FIGS. 2 and 9, the guide wire 18 extends from the proximal end 26 of the subject guide extension catheter system 10 through the internal lumen 108 in the inner member 36 within the sheath 70 and through the distal tip 102 of the inner member 36, and exits at the distal end 132 of the micro-catheter 106 of the inner member 36.

In order to provide passage to the guidewire 18, the inner member 36 has an internal lumen 108 extending along the entire inner member 36 from its proximal end 56 of the interconnection unit 50 along the internal lumen 128 extending within the sheath 70, through the length of the distal tip 102 and the length of the micro-catheter 106.

The outer tip 100 of the sheath 70 is a cone-shaped configuration made of a flexible material to facilitate a relative movement of the distal tip 102 (including the micro-catheter 106) of the inner member 36 when the inner member 36 is to be retracted into the outer sheath 70 through the outer tip 100 thereof, as required by the cardiac procedure.

As presented in FIGS. 6 and 9, the distal tip 102 of the inner member 36 which interfaces with the outer tip 100 of the sheath 70 is provided with notches 110 formed along the distal tip 102's surface so that the distal part of the outer tip 100 of the sheath 70 can be snugly received in the notches 110 of the distal tip 102 to provide a smooth transition between the outer surface of the sheath 70 and the outer surface of the distal tip 102 of the inner member 36. The notches 110 may extend along the entire length of the inner member 36, i.e., from the distal tip 102 to (and including) on the outer surface of the interconnection unit 50, or a portion of the length of the inner member 36. When the inner member 36 is pulled into the sheath 70, as required by the procedure, the flexible end 111 of the outer tip 100 stretches, and the distal tip 102 of the inner member 36, along with the micro-catheter 106 can be retracted into the outer member 40.

Figure 7:
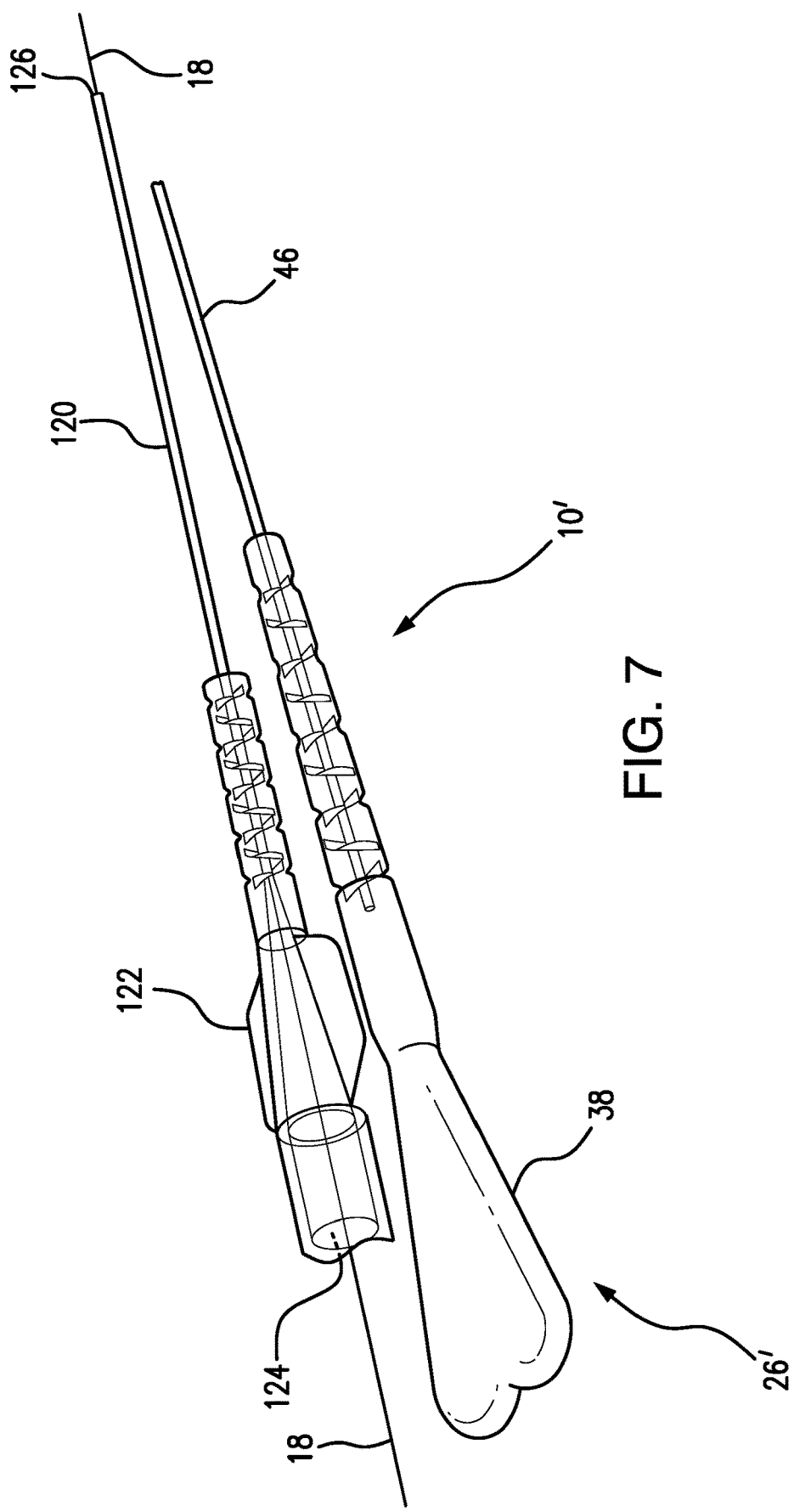
FIG. 7 depicts the proximal end of an alternative embodiment of the subject guiding catheter system.

In addition to the mono-rail design embodiment of the subject guiding extension catheter extension system 10 shown in FIG. 2, in an alternative over-the-wire (OTW) embodiment of the subject system 10', the guidewire 18 extends at the proximal end 26' of the system 10' in parallel to the inner pusher 42, as presented in FIGS. 7 and 8.

As shown in FIGS. 7 and 8, the proximal end 26' of the subject system 10' includes an inner pusher 120 formed as a tubular member having a hollow passage 121 formed therealong. In this embodiment, the inner member proximal handle 122 is configured with a passage 124 cooperating with the hollow passage 121 within the inner member pusher 120. The guidewire 18 enters the passage 124 in the inner member proximal handle 122 and extends through the hollow passage 121 of the inner member pusher 120.

The middle junction portion 30' (shown in FIG. 8) of the subject guide extension catheter system 10' is modified in comparison with the middle junction portion 30 of the system 10 shown in FIGS. 4 and 5. As shown in FIG. 8, a tubular member 126 receives the inner member pusher 120 in its internal channel for passage therealong, and leads the pusher 120 into the lumen 58 of the interconnection unit 50.

The guidewire 18 extends internally (along the hollow passage 121) in the pusher 120, within the tubular member 126, inside the interconnection member 50, and further within the inner member 36's length 138 inside the sheath 70 to the distal end 28 of the system 10', and egresses the micro-catheter 106 at the distal tip 102 of the inner member 36 similar to the guide extension catheter system 10, as shown in FIGS. 2, 6, and 9.

Referring again to FIG. 9, which shows a cross-section of the distal end 28 of the subject guide extension catheter system 10 on a somewhat enlarged scale, as well as to FIG. 6, the distal tip 102 of the inner member 36 extends along the inner channel 128 of the tubular body 72 of the sheath 70 and beyond the distal end 98 of the sheath 70. As shown, the distal tip 102 of the inner member 36 has a tapered conical configuration decreasing in diameter beginning from the distal end 98 of the sheath 70 to the distal end 104 of the distal tip 102 and is integral with the micro-catheter 106 extending beyond the distal end 104 of the distal tip 102.

As shown in FIGS. 2 and 9, the inner member 36 has an internal channel 108 which extends from the end 54 of the tubular part 52 through the length 138 of the inner member 36, through the distal tip 102 of the inner member 336, and along the micro-catheter 106 at the distal end 28 and ends at the distal end 132. The internal channel 108 of the inner member 36 thus is formed by the lumen 60 of the tubular part 52 (shown in FIGS. 4 and 4A), followed by the lumen 58 of the interconnection unit 50 (shown in FIGS. 4 and 4B-4C), as well as the internal channel 130 of the distal tip 102 and the internal channel 136 of the micro-catheter 106, and by the channel extending the length 138 (shown in FIG. 2) of the inner member 36.

The guidewire 18 is received within the internal channel 108 of the inner member 36 and extends, as required by the procedure, from the proximal end 26 through the middle junction 30 and through the distal tip 102 of the inner member 36 and along the micro-catheter 106, where it exits from the micro-catheter 106 at its distal end 132.

The distal end 98, as well as the outer tip 100 of the sheath 70, are formed of a flexible material which permits easy extension and retraction of the distal tip 102 of the inner member 36 therethrough. The flat wire helical coil may be used for the distal end 98 and the outer tip 100 of the sheath 70.

The distal tip 102 of the inner member 36 at its wider diameter has the same dimension as the diameter of the outer tip 100 of the sheath 70 in order to form a substantially smooth outer surface at the distal end 28 of the system 10. An important aspect of the subject system is that for a transition between the outer diameter of the outer tip 100 of the sheath 70 and the outer diameter of the distal tip 102 of the inner member 36 is equal to or less than 0.0006" to form substantially flush transition therebetween.

As can be seen in FIG. 9, the interface 111 between the outer tip 100 of the sheath 70 and the distal tip 102 of the inner member 36 is chamfered to facilitate displacement of the distal tip 102 of the inner member 36 relative to the outer tip 100 of the sheath 70 and basically to facilitate extension of the distal tip 102 beyond and removal from relative to the outer tip 100 of the sheath 70, as required by the cardiac procedure.

Shown in FIG. 9, it is important that the interface 111 between the outer tip 100 of the sheath 70 and the distal tip 102 of the inner member 36 has an approximate 45° chamfer. Additionally, the interface 111 has an approximate 60° chamfer formed between the outer tip 100 of the sheath 70 and the distal tip 102 of the inner member 36. The angled chamfer is for easing the displacement of the inner member 36 into the distal end 98 of the sheath 70.

As shown in FIGS. 2, 4, 5, and 8, the guide extension catheter system 10 includes interconnection unit 50 which is frictionally engaged with the inner surface 74 of the tubular body 72 of the sheath 70 at its proximal end 76. A similar frictional engagement mechanism may be provided also between the outer tip 100 of the sheath 70 and the distal tip 102 of the inner member 36 at the distal end 28 of the guide extension catheter system 10. This frictional interconnection between the inner member 36 and the outer member 40 permits the integral manipulation of both the inner member 36 and outer member 40, as required by the cardiac procedure.

Referring to FIGS. 10, 10A, 11, and 12A-12B, an alternative embodiment of the middle junction portion 30' of the subject system includes a "threaded" engagement between the interconnection unit 140 and the sheath 148. In the embodiment shown in FIGS. 10, 10A, 11 and 12A-12B, the interconnection unit 140 (which replaces the interconnection unit 50 supporting the friction engagement mechanism) is configured with an engagement button 142 extending beyond the surface 144 of the interconnection unit 140. In order to interface the interconnection unit 140 and to provide the threaded engagement between its surface 144 and the sheath 148, the proximal end 149 of the sheath 148 is modified (as compared to the sheath 70 adapted for the frictional engagement) and is configured with a system of flexible ribs 150 separated by respective inter-rib spaces 152 which extend in a somewhat arcuated configuration reflecting the cylindrical configuration of the sheath 148 and are adapted to embrace the cylindrically shaped outer surface 144 of the unit 140.

One of the inter-rib spaces 152, specifically, the slot-like portion 154 is shaped with an exit channel 156 angularly cooperating at one of its ends 158 with the engagement slot 160.

Figure 12:
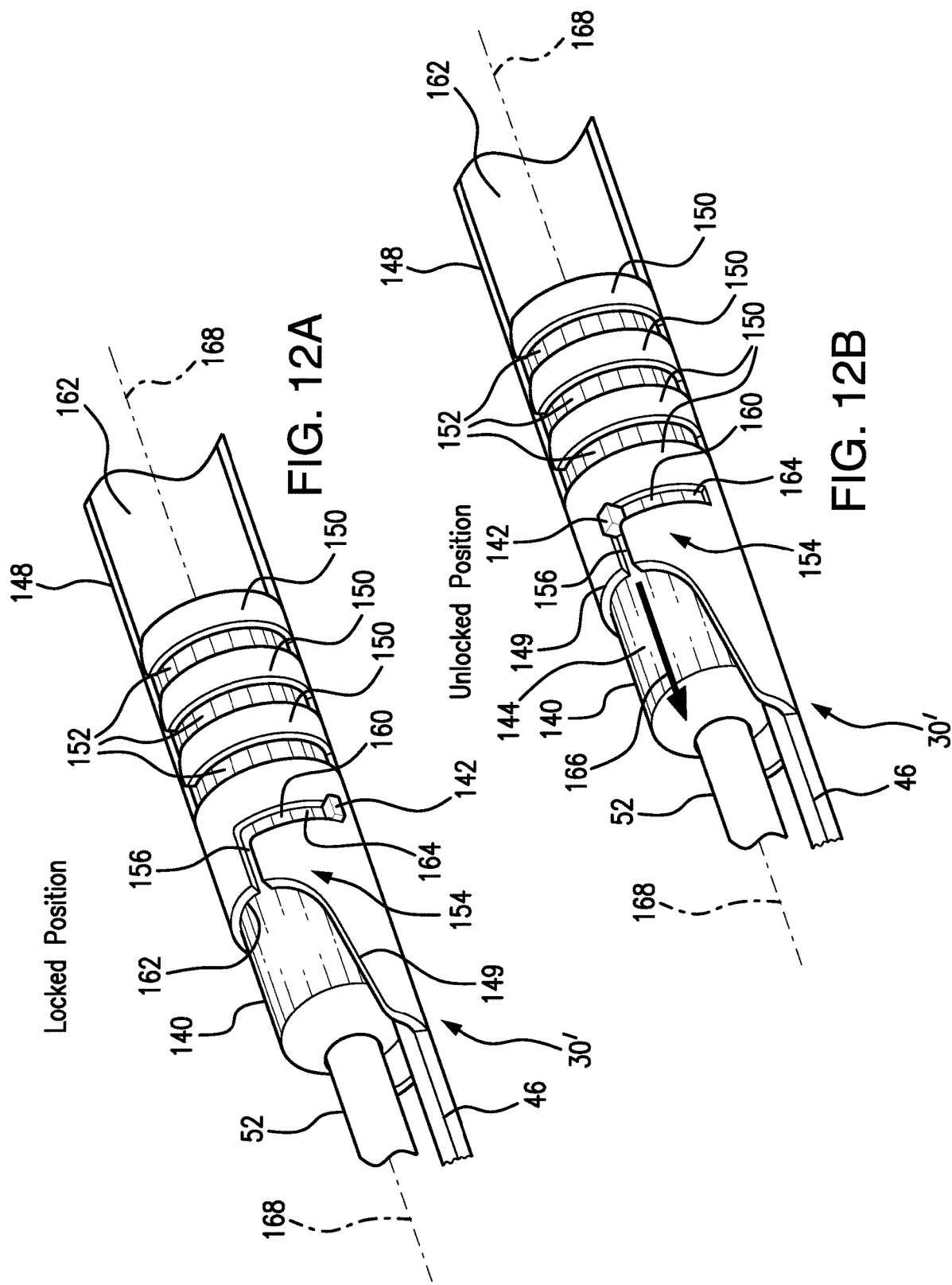
FIGS. 12A and 12B depict the threaded assembly of the middle junction of the subject system in its locked position (FIG. 12A) and unlocked position (FIG. 12B)

In the arrangement shown in FIGS. 10, 10A, 11, and 12A-12B, when the inner member 36 is to be engaged with the outer member 40, specifically by coupling the interconnection unit 140 to the proximal end 149 of the sheath 148, the interconnection unit 140 is extended (by a surgeon forward-pushing the inner member pusher 42) into the lumen 162 of the sheath 148 at its proximal end 149, so that the engagement button 142 on the surface 144 of the interconnection unit 140 moves along the exit channel 156 to the end 158 thereof. At this instance, a surgeon (operator) turns the inner member 36 in clockwise direction toward its end 164 (by manipulating the inner member pusher 42) to advance the engagement button 142 along the engagement slot 160 as shown in FIG. 12A for locking the inner member 36 with the outer member (i.e., the sheath 148). When the engagement button 142 is placed at the end 164 of the engagement slot 160, the inner and outer members, 36 and 40, respectively, are placed in the locked position, as shown in FIG. 12A.

In order to unlock (disengage) the inner member 36 from the outer member 40, as shown in FIG. 12B, the engagement button 142 is displaced (by a surgeon manipulating the inner member pusher 42) from the end 164 along the engagement slot 160 towards the end 158 of the exit channel 156 (by a surgeon manipulating the pusher 42 to make a counter-clockwise rotation of the inner member 36 relative to the outer member 40). Subsequently, the inner member 36 is pulled from the sheath 148 (by pulling the inner member pusher 42) with the engagement button 142 moving along the exit channel 156 from the end 158 thereof in the direction shown by the arrow 166. When the engagement button 142 is removed from the exit channel 156, the inner member 36 is disengaged (or unlocked) from the sheath 148, as depicted in FIG. 12B.

In order to linearly displace the interconnection unit 140 into or from the sheath 148, or to rotate the interconnection unit 140 in clockwise or counter-clockwise direction about the longitudinal axis 168 of the system, a surgeon (operator) uses the inner member pusher 42 which is either molded (glued, welded, or otherwise fixedly attached to the interconnection unit 50 or 140, as presented in the embodiments of FIGS. 4-4C, 5, and 10), or which is attached to the internal lumen of the interconnection unit 140, similar to the embodiment shown in FIG. 8.

Figure 13:
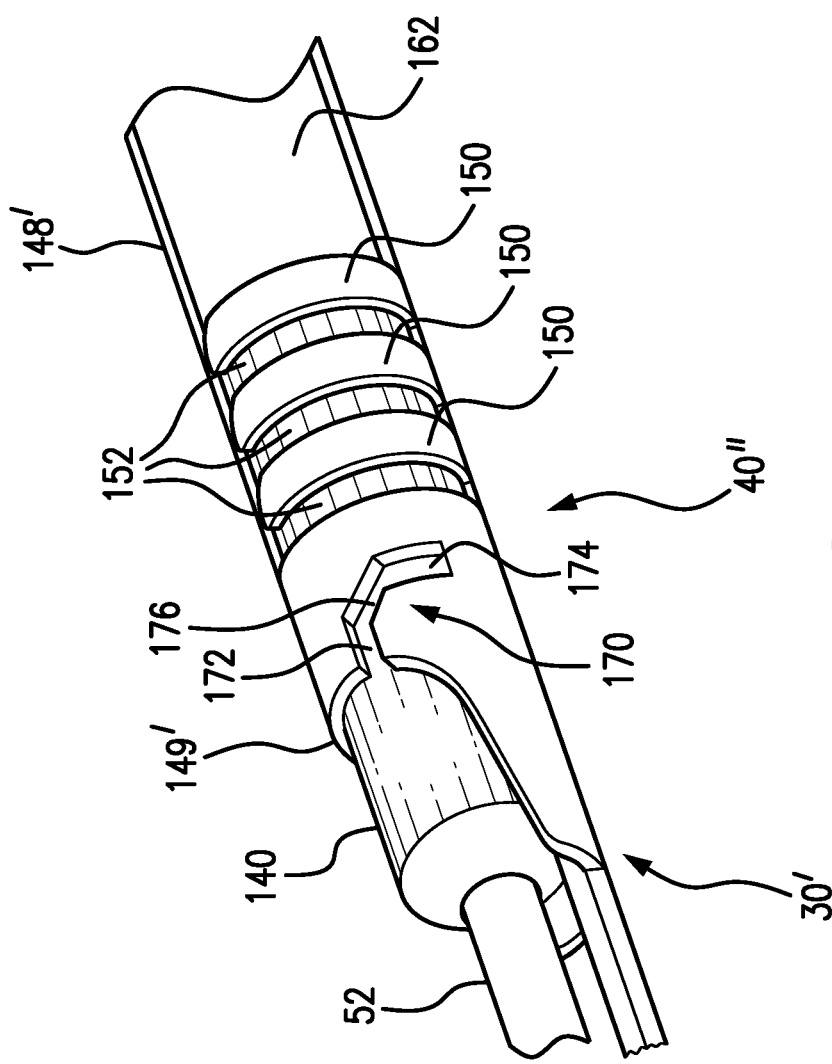
FIG. 13 depicts the alternative embodiment of the middle junction of the subject system designed with a modified engagement mechanism.

FIG. 13 shows a further alternative embodiment of the proximal end 149' of the sheath 148 which is shown slightly modified in comparison with FIGS. 11 and 12A-12B. Specifically, the exit channel/engagement slot 160 shown in FIGS. 12A and 12B is replaced with an engagement channel 170 where the substantially perpendicular relationship between the exit channel 156 and the engagement slot 160 is replaced with a somewhat 45° angled configuration where the exit channel 172 and the ending engagement slot 174 are connected by a substantially flat interconnection channel 176. The interconnection channel 176 is similarly angled about 45° with relation to the exit channel 172 and the ending engagement slot 174. This arrangement provides a mechanical advantage for engaging the engagement button 142 in the engagement channel 170, and prevents accidental disengagement of the engagement button 142 from the engagement channel 170.

Figure 14:
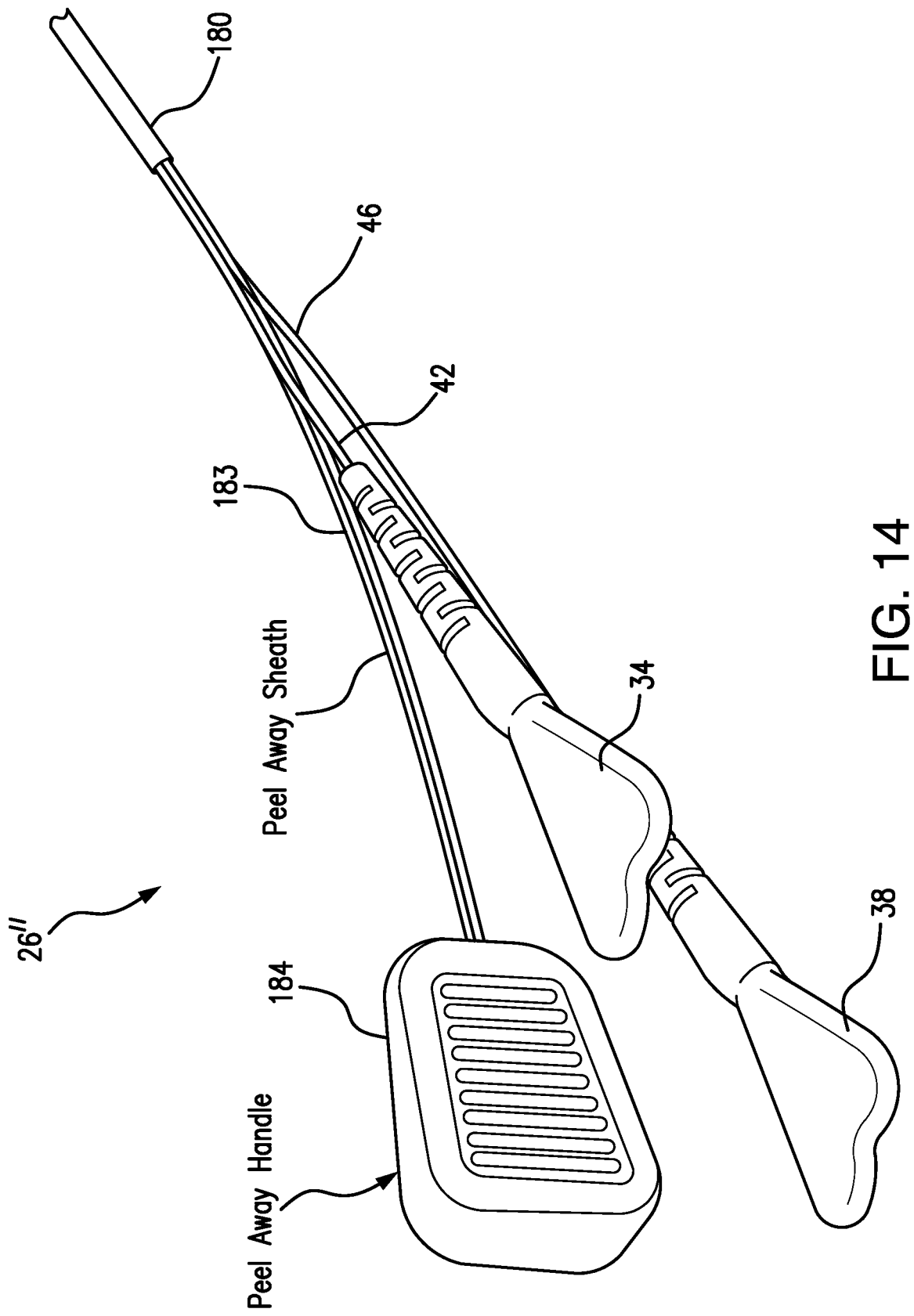
FIG. 14 depicts a peel-away embodiment of the subject system.
Figure 15:
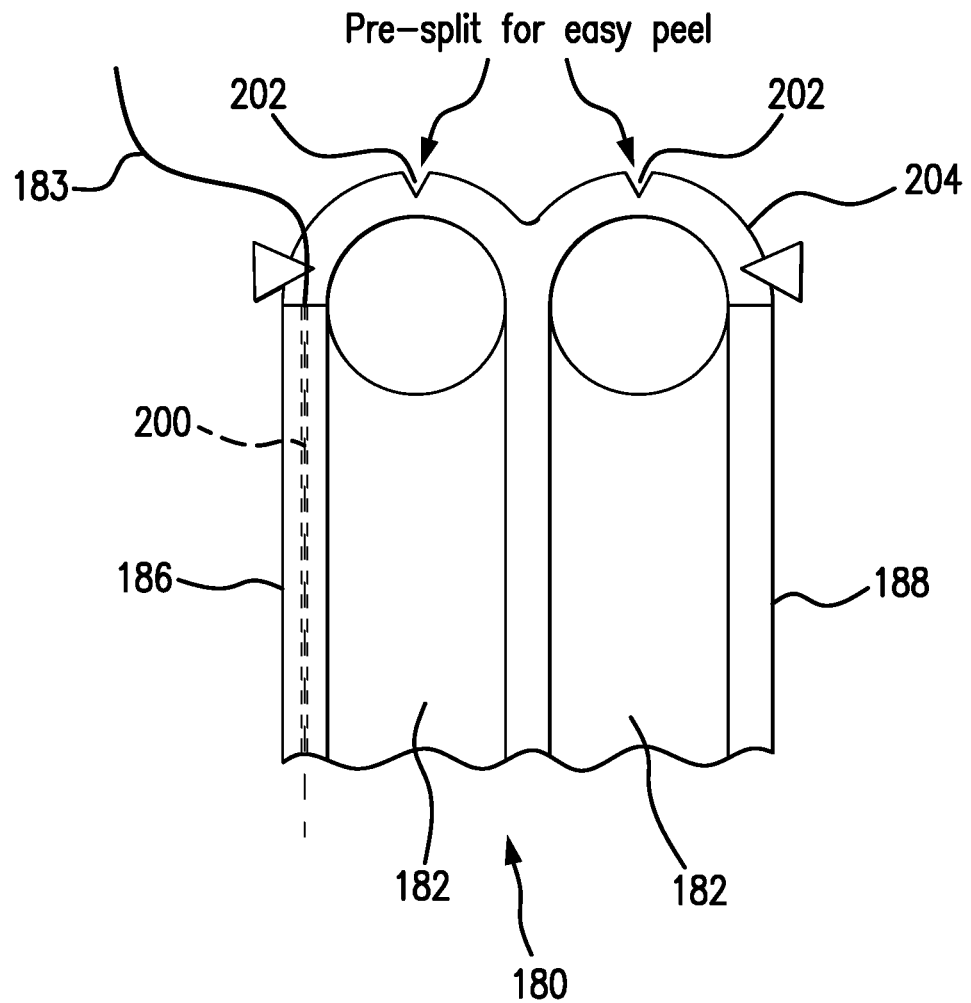
FIG. 15 shows schematically the details of the peel-away embodiment of the subject system.

In another embodiment of the engagement/disengagement mechanism between the inner member 36 and outer member 40, shown in FIGS. 14-15, in the engaged mode of operation, the inner member pusher 42 and the outer member pusher 46 are positioned in a single peel away sheath 180 having a channel 182 where both inner and outer pushers extend in connection one with another. The peel away sheath 180 is connected to the peel away handle 184 by a cord 183. The sheath 180 (as shown in FIG. 15) is pre-cut at its sides 188, and the sides are held together, to form the channel 182, by a wire/suture 200 embedded therein. The wire/suture 200 is operatively connected to the handle 184 by a cord 183.

When disengagement of the inner and outer members 36, 40 is required (in the case of extending the inner member 36 with regard to the outer member 40, or pulling the inner member 36 into and from the outer member 40), a surgeon manipulates a peel away handle 184 to pull the cord 183. Having been pulled, the cord 183 applies the force to a wire/suture 200 embedded in the side(s) 186, 188 of the sheath 180. As a result, the wire/suture 200 breaks, and the sheath 180 "opens" at the side(s) 186, 188. At this moment, the peel away sheath 180 is divided into two halves when the side 186 is separated from the side 188, and the inner and outer member pushers 42, 46 are "freed" from the sheath 180, and can be manipulated independently of each other. As a result, the inner member 36 is disengaged from the outer member 40 (i.e., the sheath 70) for a controlled displacement relative thereto.

The peel away sheath 180 may also have several serrations 202 along its surface 204 for facilitating an easy splitting of the sides 186, 188 (or at other locations along the surface 204) of the peel away sheath 180.

Figure 16B:
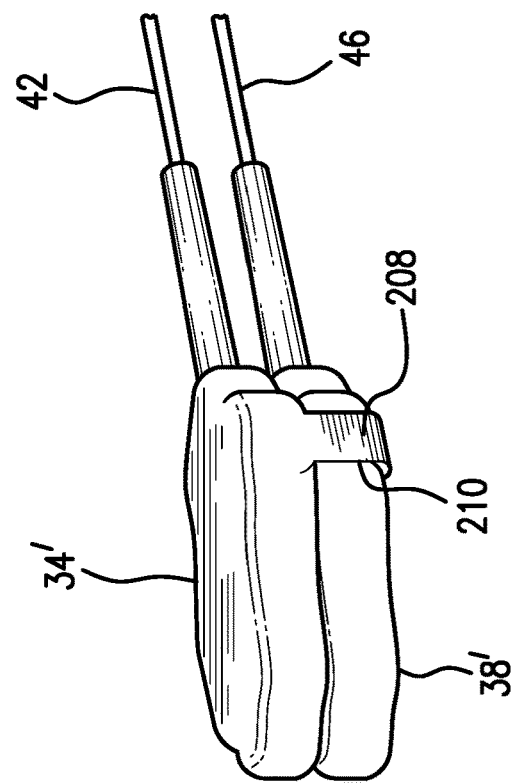
FIGS. 16A-16B show the "snap-together hubs" alternative embodiment of the subject system with FIG. 16A depicting the inner and outer pusher hubs disengaged, and FIG. 16B depicting the inner and outer usher hubs engaged.
Figure 16A:
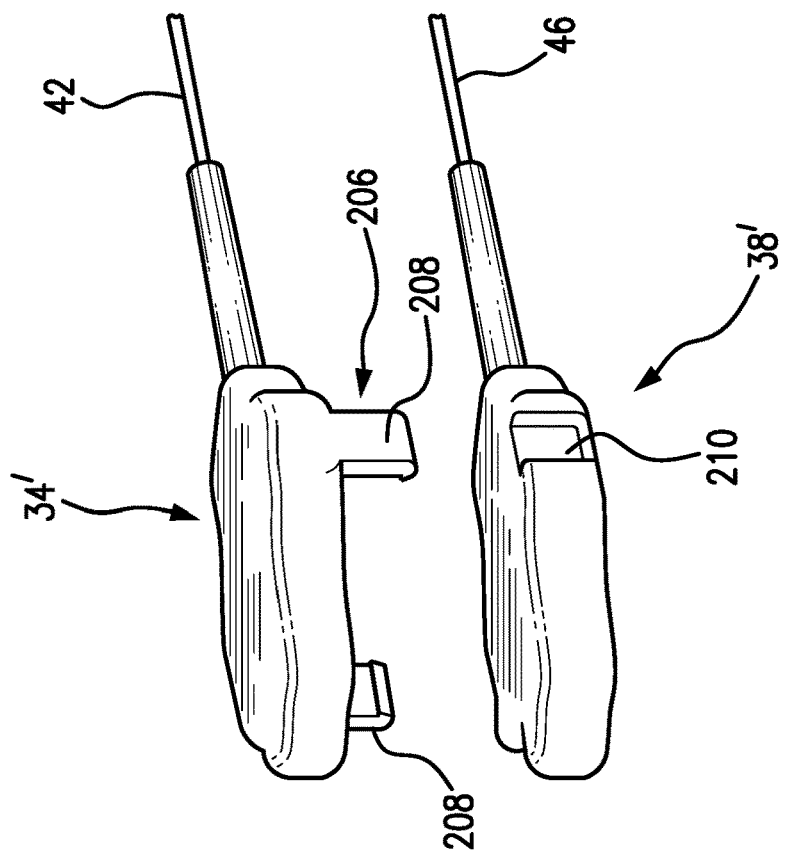

Referring to FIGS. 16A-16B, an additional embodiment of the engagement/disengagement mechanism includes the handles 34' and 38' of the inner and outer member pushers 42, 46, respectively, which may be attached, as shown in FIG. 16B to provide an integral motion together as a single unit during the procedure. As shown in FIG. 16A, the handles 34', 38' are disengaged to provide a relative displacement of the inner and outer members 36, 40, respectively, as required during the cardiac procedure.

In order to provide an engagement/disengagement of the inner member 36 and the outer member 40, respectively, the handles are provided with a snap mechanism 206. The snap mechanism 206 may include two tabs 208 formed on the sides of the handle 34' for the inner member 36 to be engageable with the notches 210 formed on the companion handle 38' for the outer member 40. The handles' snap mechanism 206 is just one exemplary mechanism of many envisioned for engagement/disengagement between the inner and outer members in the subject system.

In operation, as shown in FIG. 17A, for performing the cardiac procedure, a proximal end of the coronary guidewire 18 is extended through the inner channel 108 of the inner member of the subject system 10. Subsequent thereto, the guide catheter 11, along with a guidewire 18 therewithin, is inserted and advanced into the blood vessel 16 of interest. At this stage, the distal end 24 of the guide catheter is not placed at the lesion location 20.

Subsequently, the sheath 70, locked with the inner member 36 therewithin, is advanced within the guide catheter 11 towards the treatment site 20 and reaches the distal end 24 of the guide catheter 11.

Further, as shown in FIG. 17B, the guidewire 18 which extends beyond the distal end 24 of the guide catheter 11, serves as a guide along which the micro-catheter 106 slides towards the treatment site 20. During this step of the cardiac procedure, the sheath 70 is disengaged from the inner member 36 by any mechanism described in previous paragraphs. Thus, the distal tip 102 (particularly, the micro-catheter 106) of the inner member 36 is advanced beyond the distal end of the sheath 70, along the blood vessel 16 towards (or beyond) the lesion 20 to be treated, as shown in FIG. 17C.

Subsequently, as shown in FIG. 17D, the sheath 70 is pushed by the surgeon to slide inside the guide catheter 11 along the micro-catheter 106 towards or beyond the lesion 20. Once the distal end 98 of the sheath 70 reaches or passes beyond the lesion 20, the inner member 36 is removed from the sheath 70. At this stage, the distal end 98 of the sheath 70 (within the guide catheter 11) is positioned in alignment or beyond the lesion 20 and remains within the guide catheter 11.

As further shown in FIG. 17E, upon removal of the inner member 36, a stent delivery system or a balloon catheter 230 can be delivered to the lesion 20 for a subsequent treatment.

Another embodiment of this same invention describes the use of a similar micro-catheter delivery system that is placed inside a balloon expandable guide extension tube to allow one to deliver the micro-catheter tip and a low profile guide extension catheter to an area beyond a lesion of interest and then to use a balloon contained on the outer aspect of the micro-catheter to mechanically expand a metal reinforced but balloon expandable guide extension tube after it has been already delivered at a lower profile diameter to the area at or distal to a lesion to be treated. In this way, one can deliver a guide extension system that is ~4-5 French (1.3-1.6 mm) in outer diameter and 3-4 French in inner diameter, and then balloon expand this tubular structure to be 5-6 French (1.6-2.0 mm) in inner diameter after it has been delivered as a lower profile catheter to the appropriate distal location.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. An intravascular system the intravascular system comprising:
    a guide wire removably advanceable in a blood vessel of interest to at least a treatment site; and
    a guide catheter extension sub-system configured for controllable displacement along the guide wire, the guide catheter extension sub-system having a proximal portion, a distal portion, and a middle junction portion interconnected between the proximal and distal portions,
    wherein the guide catheter extension sub-system comprises:
        an outer member formed by a flexible substantially cylindrically contoured elongated sheath defining a sheath lumen having a proximal end and a distal end, the flexible substantially cylindrically contoured elongated sheath extending between the middle junction portion and the distal portion of the guide catheter extension sub-system, wherein the distal end of the flexible substantially cylindrically contoured elongated sheath is configured with a tapered outer tip having an inner diameter,
        a flexible inner member having an elongated body defining an internal channel extending along a longitudinal axis of the elongated body, the flexible inner member extending internally along the sheath lumen in a controllably displaceable relationship with the flexible substantially cylindrically contoured elongated sheath, wherein the flexible inner member has a tapered delivery micro-catheter integral with and forming a distal end of the flexible inner member configured with a tapered distal tip, the flexible inner member having a first portion and a second portion, the first portion being contiguous with the flexible substantially cylindrically contoured elongated sheath throughout a length of the first portion of the flexible inner member between a proximal end of the flexible inner member and the second portion of the flexible inner member devoid of a gap therebetween, wherein the first portion of the flexible inner member has an outer diameter less than an outer diameter of the second portion of the flexible inner member, and wherein the outer diameter of the second portion of the flexible inner member exceeds the inner diameter of the tapered outer tip of the flexible substantially cylindrically contoured elongated sheath, wherein the tapered delivery micro-catheter has an elongated body of a predetermined length, wherein the tapered delivery micro-catheter is displaceable along the guide wire beyond the distal end of the sheath lumen, and wherein a flexibility of the tapered micro-catheter increases from a proximal end to a distal end of the tapered micro-catheter, and an inner member pusher coupled, at a distal end of the inner member pusher, to the proximal end of the flexible inner member, and an outer member pusher coupled, at a distal end of the outer member pusher, to the proximal end of the sheath lumen, wherein the inner member pusher and the outer member pusher are formed at the proximal portion of the guide catheter extension sub-system and are actuated to control displacement of the flexible inner member and the outer member along the guide wire, wherein the inner member pusher and the outer member pusher are solid wires, wherein the distal end of the inner member pusher is tapered, and wherein the flexible inner member includes, at the proximal end of the flexible inner member, a tubular member having a proximal opening and an internal channel aligned with the internal channel of the flexible inner member, and wherein the guide wire and the tapered distal end of the inner member pusher are received in the internal channel of the tubular member through the proximal opening for extending along the internal channel of the tubular member substantially in parallel relationship; and an interconnection mechanism disposed in an operative coupling with the flexible inner member and the outer member of the guide catheter extension sub-system and controllably actuated to operate the guide catheter extension sub-system intermittently in an engaged mode of operation and a disengaged mode of operation;

wherein, in the engaged mode of operation, the flexible inner member and the outer member of the guide catheter extension sub-system assume an engaged configuration for a controllable common displacement along the guide wire with the tapered outer tip of the flexible substantially cylindrically contoured elongated sheath interfacing the tapered distal tip of the flexible inner member with a substantially flush transition between an outer surface of the tapered distal tip of the flexible inner member and an outer surface of the tapered outer tip of the flexible substantially cylindrically contoured elongated sheath, and wherein, in the disengaged mode of operation, the flexible inner member and the outer member assume a disengaged configuration for a controllable individual linear or rotational displacement relative one another, and wherein, when the flexible inner member is displaced relative the flexible substantially cylindrically contoured elongated sheath, the tapered outer tip of the flexible substantially cylindrically contoured elongated sheath is elastically stretchable to permit passage of the second portion of the flexible inner member through the tapered outer tip of the flexible substantially cylindrically contoured elongated sheath for displacement of the flexible inner member and the outer member each with respect to the other.

2. The intravascular system of claim 1, wherein the tapered micro-catheter is formed of a flexible material having differential flexibility along the length of the tapered micro-catheter.

3. The intravascular system of claim 2, wherein the tapered micro-catheter includes a flat wire helical coil extending along the elongate body of the predetermined length of the tapered micro-catheter, and wherein a pitch of the flat wire helical coil changes along the length of the tapered micro-catheter to increase the flexibility of the tapered micro-catheter towards the distal end of the tapered micro-catheter.

4. The intravascular system of claim 1, wherein the elongate body of the predetermined length of the tapered micro-catheter is greater than 2 cm.

5. The intravascular system of claim 1, wherein a diameter of the tapered micro-catheter at the distal end of the tapered micro-catheter is less than 1 mm.

6. The intravascular system of claim 1, wherein the tapered distal tip of the flexible inner member interfaces, at an outer surface of the flexible inner member, with an inner surface of the tapered outer tip of the flexible substantially cylindrically contoured elongated sheath, and wherein a dimensional transition between an outer diameter of the tapered outer tip of the flexible substantially cylindrically contoured elongated sheath and an outer diameter of the tapered distal tip of the flexible inner member is less than 0.006 inch.

7. The intravascular system of claim 1, wherein the guide catheter extension sub-system further includes:

an inner member pusher handle, and an outer member pusher handle;

wherein the inner member pusher is attached, at a proximal end of the inner member pusher, to the inner member pusher handle, and wherein the outer member pusher is attached, at a proximal end of the outer member pusher, to the outer member pusher handle.

8. The intravascular system of claim 7, wherein the interconnection mechanism is operatively coupled to the inner and outer member pusher handles, the interconnection mechanism including tabs extending at opposite sides of one of the inner and outer member pusher handles, and notches formed at respective sides of another one of the inner and outer member pusher handles, the tabs disengageably cooperating with the notches, thus forming a snap-based interconnection mechanism.

9. The intravascular system of claim 1, wherein the interconnection mechanism includes a friction-based mechanism created between an outer surface of the flexible inner member and an inner surface of the flexible substantially cylindrically contoured elongated sheath of the outer member.

10. The intravascular system of claim 1, wherein the interconnection mechanism includes a threaded engagement/disengagement mechanism configured with at least one engagement button extending above an external surface of the flexible inner member, and at least one engagement slot configured at least at the proximal end of the sheath lumen of the outer member, the at least one engagement button being removably engaged in the at least one engagement slot in the engaged mode of operation for locking the flexible inner member and the outer member to one another.

11. The intravascular system of claim 10, wherein the at least one engagement slot is configured with a first channel and a second channel extending substantially perpendicular to one another, and a third channel extending in communication with the first and second channels in an angled relationship with the first and second channels.

12. The intravascular system of claim 1, wherein the interconnection mechanism includes:

a pull-away sheath formed with a substantially cylindrically shaped body having a wall defining an internal channel for receiving the inner and outer member pushers therein in the engaged mode of operation, the wall being pre-treated for collapsing therealong, and a cord in operative coupling, at one end thereof, with the wall, the cord being pullable to break the wall in the disengaged mode of operation, thus disengaging the inner member pusher from the outer member pusher, thereby unlocking the flexible inner member from the outer member.

13. The intravascular system of claim 1, wherein the guide catheter extension sub-system further includes a flat wire helical coil member forming at least a portion of respective walls of a member selected from a group including the flexible substantially cylindrically contoured elongated sheath, the tapered micro-catheter, and combination thereof.

14. The intravascular system of claim 1, wherein the tubular member includes a reinforced portion formed with a flat wire helical coil embedded in a wall of the tubular member and extended circumferentially around the internal channel of the tubular member.

15. The intravascular system of claim 14, wherein the flat wire helical coil member is formed with a shape memory alloy including Nitinol.

16. The intravascular system of claim 14, wherein the flat wire helical coil member is formed of a radio-opaque material.

17. The intravascular system of claim 1, further including radio-opaque markers attached to at least the distal end of the sheath lumen of the flexible substantially cylindrically contoured elongated sheath and the distal end of the tapered micro-catheter.

18. The intravascular system of claim 1, wherein the distal end of the outer member pusher has a tapered arcuated arcuate configuration cooperating with a contour of the flexible inner member at the proximal end of the flexible inner member, the distal end of the outer member pusher being fixedly attached to the flexible substantially cylindrically contoured elongated sheath at the proximal end of the sheath lumen.

19. An intravascular system equipped comprising:
a guide wire removably advanceable in a blood vessel of interest to at least a treatment site; and
a guide catheter extension sub-system configured for controllable displacement along the guide wire, the guide catheter extension sub-system having a proximal portion, a distal portion, and a middle junction portion interconnected between the proximal and distal portions,
wherein the guide catheter extension sub-system comprises:
an outer member formed by a flexible substantially cylindrically contoured elongated sheath defining a sheath lumen having a proximal end and a distal end, the flexible substantially cylindrically contoured elongated sheath extending between the middle junction portion and the distal portion of the guide catheter extension sub-system;
a flexible inner member having an elongated body defining an internal channel extending along a longitudinal axis of the elongated body, the flexible inner member extending internally along the sheath lumen in a controllably displaceable relationship with the flexible substantially cylindrically contoured elongated sheath, said sheath, wherein the flexible inner member has a tapered delivery micro-catheter integral with and forming a distal end of the flexible inner member, the tapered delivery micro-catheter having an elongated body of a predetermined length, wherein the tapered delivery micro-catheter is displaceable along the guide wire beyond the distal end of the sheath lumen, and wherein a flexibility of the tapered micro-catheter increases from a proximal end to a distal end of the tapered micro-catheter, the flexible inner member having a first portion and a second portion with a length of the first portion being contiguous with the flexible substantially cylindrically contoured elongated sheath throughout a length of the first portion of the flexible inner member between a proximal end of the flexible inner member and the second portion of the flexible inner member, and wherein an outer diameter of the second portion of the flexible inner member exceeds an inner diameter of a tapered end of the flexible substantially cylindrically contoured elongated sheath; and,
an interconnection mechanism disposed in an operative coupling with the flexible inner member and the outer member of the guide catheter extension sub-system and controllably actuated to operate the guide catheter extension sub-system intermittently in an engaged mode and a disengaged mode of operation, wherein, in the engaged mode of operation, the inner flexible member and the outer member of the guide catheter extension sub-system are engaged for a controllable common displacement along the guide wire, and wherein, in the disengaged mode of operation, the inner flexible member and the outer member are disengaged for a controllable individual linear or rotational displacement relative one another;
wherein the interconnection mechanism includes a first engagement portion configured at the proximal end of the flexible substantially cylindrically contoured elongated sheath of the outer member and a second engagement portion configured at an outer surface of a proximal portion of the elongated body of the flexible inner member, wherein the first engagement portion of the interconnection mechanism includes at least one primary rib, at least one secondary rib distal to the at least one primary rib, and an exit channel formed at the proximal end of the flexible substantially cylindrically contoured elongated sheath in communication with the at least one primary rib for removal of the flexible inner member from the flexible substantially cylindrically contoured elongated sheath, the at least one secondary rib having a split ring configuration having at least a pair of flexible arcuately contoured arms circumferentially aligned each with respect to the other,
wherein, in the engaged mode of operation, the second engagement portion of the interconnection mechanism is engaged in the at least one primary rib, and the proximal portion of the elongated body of the flexible inner member is received inside the split ring configuration of the at least one secondary rib with the two arcuately contoured arms thereof flexibly embracing the proximal portion of elongated body of the flexible inner member,
wherein, in the disengaged mode of operation, the interconnection mechanism supports a displacement of the flexible inner member within or from the flexible substantially cylindrically contoured elongated sheath of the outer member, and
wherein, in the engaged mode of operation, the interconnection mechanism prevents the distal motion and restricts the proximal motion of the flexible inner member within the outer member such that the flexible inner member is capable of retraction in the proximal direction by exertion of a force greater than that required to retract the flexible inner member when the interconnection mechanism is in the disengaged mode of operation.

20. The intravascular system of claim 19, wherein the tapered micro-catheter is formed of a flexible material having differential flexibility along the length of the tapered micro-catheter.

21. The intravascular system of claim 20, wherein the tapered micro-catheter includes a flat wire helical coil extending along the elongate body of the predetermined length of the tapered micro-catheter, and wherein a pitch of the flat wire helical coil changes along the length of the tapered micro-catheter to increase the flexibility of the tapered micro-catheter towards the distal end of the tapered micro-catheter.

22. The intravascular system of claim 19, wherein the elongate body of the predetermined length of the tapered micro-catheter is greater than 2 cm.

23. The intravascular system of claim 19, wherein a diameter of the tapered micro-catheter at the distal end of the tapered micro-catheter is less than 1 mm.

24. The intravascular system of claim 19, wherein the tapered distal tip of the flexible inner member interfaces, at an outer surface of the flexible inner member, with an inner surface of the tapered outer tip of the flexible substantially cylindrically contoured elongated sheath, and wherein a dimensional transition between an outer diameter of the tapered outer tip of the flexible substantially cylindrically contoured elongated sheath and an outer diameter of the tapered distal tip of the flexible inner member is less than 0.006 inch.

25. The intravascular system of claim 19, wherein the guide catheter extension sub-system further comprises:
   an inner member pusher coupled, at a distal end of the inner member pusher, to a proximal end of the flexible inner member, and
   an outer member pusher coupled, at a distal end of the outer member pusher, to the proximal end of the sheath lumen;
   wherein the inner and outer member pushers are formed at the proximal portion of the guide catheter extension sub-system and are actuated to control displacement of the flexible inner member and the outer member along the guide wire.

26. The intravascular system of claim 25, wherein the guide catheter extension sub-system further includes:
   an inner member pusher handle, and
   an outer member pusher handle;
   wherein the inner member pusher is attached, at a proximal end of the inner member pusher, to the inner member pusher handle, and
   wherein the outer member pusher is attached, at a proximal end of the outer member pusher, to the outer member pusher handle.

27. The intravascular system of claim 26, wherein the inner member pusher is formed in a tubular configuration having an internal channel extending along a longitudinal axis of the inner member pusher,
   wherein the inner member pusher handle includes an entrance channel communicating with the internal channel of the inner member pusher, and
   wherein the guide wire enters into the internal channel of the flexible inner member at the proximal end of the flexible inner member through the entrance channel of the inner member pusher handle in communication with the internal channel of the inner member pusher.

28. The intravascular system of claim 25, wherein the inner member pusher and the outer member pusher are solid wires, wherein the distal end of the inner member pusher is tapered, and wherein the flexible inner member includes, at the proximal end of the flexible inner member, a tubular member having a proximal opening and an internal channel aligned with the internal channel of the flexible inner member, and
   wherein the guide wire and the tapered distal end of the inner member pusher are received in the internal channel of the tubular member through the proximal opening for extending along the internal channel of the tubular member substantially in parallel relationship.

29. The intravascular system of claim 28, wherein the tubular member includes a reinforced portion formed with a flat wire helical coil embedded in a wall of the tubular member and extended circumferentially around the internal channel of the tubular member.

30. The intravascular system of claim 29, wherein the flat wire helical coil member is formed with a shape memory alloy including Nitinol.

31. The intravascular system of claim 29, wherein the flat wire helical coil member is formed of a radio-opaque material.

32. The intravascular system of claim 25, wherein the distal end of the outer member pusher has a tapered arcuate configuration cooperating with a contour of the flexible inner member at the proximal end of the flexible inner member, the distal end of the outer member pusher being fixedly attached to the flexible substantially cylindrically contoured elongated sheath at the proximal end of the sheath lumen.

33. The intravascular system of claim 19, wherein the guide catheter extension sub-system further includes a flat wire helical coil member forming at least a portion of respective walls of a member selected from a group including the flexible substantially cylindrically contoured elongated sheath, the tapered micro-catheter, and combination thereof.

34. The intravascular system of claim 19, further including radio-opaque markers attached to at least the distal end of the sheath lumen of the flexible substantially cylindrically contoured elongated sheath and the distal end of the tapered micro-catheter.

* * * * *

UNITED STATES PATENT AND TRADEMARK OFFICE
CERTIFICATE OF CORRECTION

| | | |
|---|---|---|
| PATENT NO. | : 11,491,313 B2 | Page 1 of 1 |
| APPLICATION NO. | : 15/899603 | |
| DATED | : November 8, 2022 | |
| INVENTOR(S) | : Tim A. Fischell | |

It is certified that error appears in the above-identified patent and that said Letters Patent is hereby corrected as shown below:

In the Claims

Column 21, Line 30, Claim 18, after "tapered" delete "arcuated".

Column 21, Line 61, Claim 19, before "wherein" delete "said sheath,".

Column 22, Line 55, Claim 19, before "elongated" insert -- the --.

Signed and Sealed this
Twenty-eighth Day of February, 2023

*Katherine Kelly Vidal*

Katherine Kelly Vidal
*Director of the United States Patent and Trademark Office*